(12) United States Patent
Skender

(10) Patent No.: US 11,911,303 B2
(45) Date of Patent: Feb. 27, 2024

(54) UNIVERSAL ADAPTER FOR GRAFT ATTACHMENT TO DELIVERY SYSTEMS

(71) Applicant: Cook Medical Technologies LLC, Bloomington, IN (US)

(72) Inventor: Davorin K. Skender, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 400 days.

(21) Appl. No.: 17/150,624

(22) Filed: Jan. 15, 2021

(65) Prior Publication Data
US 2022/0226134 A1    Jul. 21, 2022

(51) Int. Cl.
*A61F 2/95*    (2013.01)
*A61F 2/07*    (2013.01)

(52) U.S. Cl.
CPC .............. *A61F 2/95* (2013.01); *A61F 2/07* (2013.01); *A61F 2002/9511* (2013.01); *A61F 2220/0075* (2013.01); *A61F 2230/0054* (2013.01); *A61F 2230/0078* (2013.01)

(58) Field of Classification Search
CPC ...... A61F 2/95; A61F 2/07; A61F 2002/9511; A61F 2220/0075; A61F 2230/0054; A61F 2230/0078
See application file for complete search history.

(56) References Cited

U.S. PATENT DOCUMENTS

| | | | |
|---|---|---|---|
| 6,565,597 B1 | 5/2003 | Fearnot et al. | |
| 7,175,652 B2 | 2/2007 | Cook et al. | |
| 7,238,198 B2 | 7/2007 | Hartley et al. | |
| 7,909,863 B2 | 3/2011 | Hartley et al. | |
| 8,343,204 B2 | 1/2013 | Osborne | |
| 9,517,123 B2 | 12/2016 | Leewood et al. | |
| 2013/0289703 A1 | 10/2013 | Kinkade et al. | |
| 2015/0164667 A1 | 6/2015 | Vinluan et al. | |
| 2018/0263753 A1 | 9/2018 | Vinluan et al. | |
| 2019/0070025 A1 | 3/2019 | Fu et al. | |
| 2020/0146806 A1 | 5/2020 | Brocker et al. | |

FOREIGN PATENT DOCUMENTS

| | | |
|---|---|---|
| FR | 2714816 A1 | 7/1995 |
| WO | WO 2003/053288 A1 | 7/2003 |
| WO | WO 2009/132309 A1 | 10/2009 |

OTHER PUBLICATIONS

Lin, Peter H. et al., Endovascular Repair of Thoracic Aortic Disease: Overview of Current Devices and Clinical Results, Disclosures, Vascular. 2007;15(4):179-190, Medscape, Wednesday, Apr. 21, 2021, 6 pp, https://www.medscape.com/viewarticle/562772_4.

Janowski, Konrad, Ph.D., Abdominal aortic aneurysm repair with Lifetech Ankura AAA stent graft system, The Ministry of Internal Affairs and Administration Hospital, Lodz, Poland, LINC, MWiA, 14 pp.

Extended European Search Report for European application No. 22275005.1, dated Jun. 1, 2022, 8 pgs.

*Primary Examiner* — Todd J Scherbel

(74) *Attorney, Agent, or Firm* — Crowell & Moring LLP

(57) ABSTRACT

A stent graft retention system for retaining a stent graft on a delivery device is provided. The stent graft retention system includes a stent graft, a stent, and a plurality of discrete retention wire forms at least one of which is configured to engage a trigger wire.

16 Claims, 20 Drawing Sheets

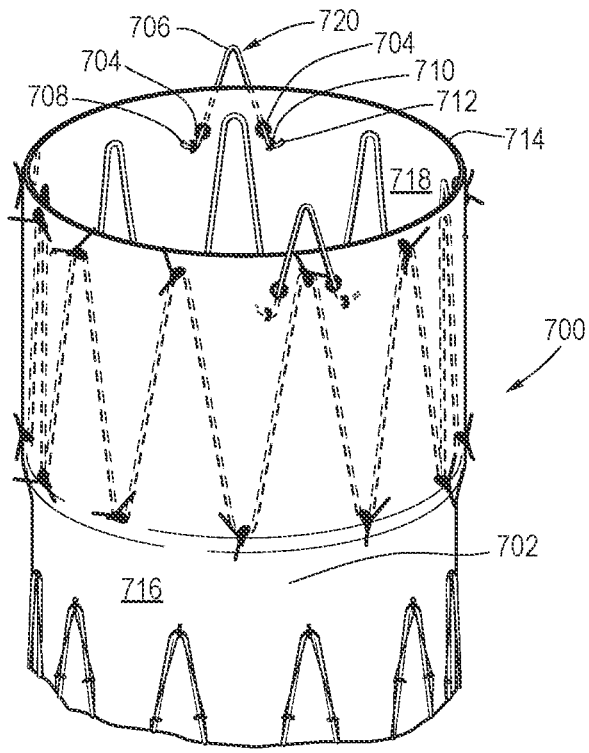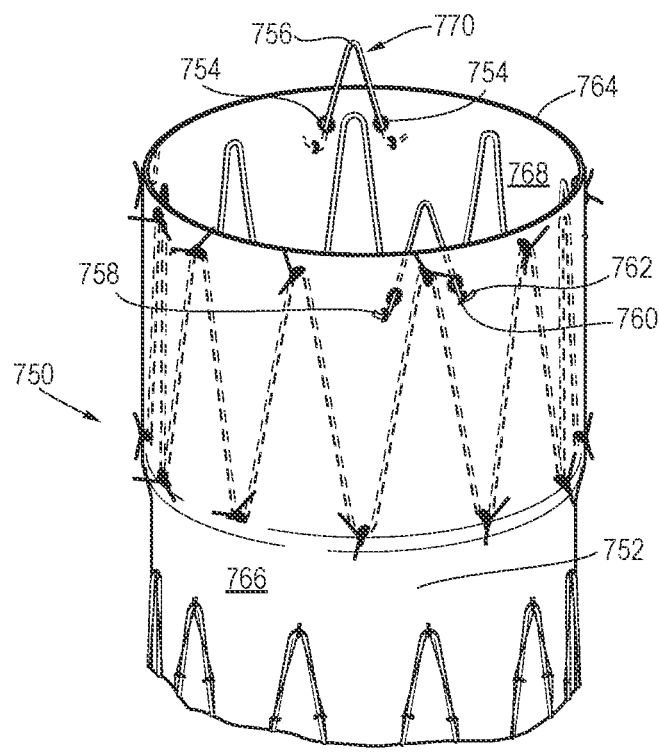

UNIVERSAL ADAPTER FOR GRAFT ATTACHMENT TO DELIVERY SYSTEMS

FIELD

The present disclosure relates to medical devices.

BACKGROUND

The statements in this section merely provide background information related to the present disclosure and may not constitute prior art.

Development of new universal delivery device systems may present design challenges for retaining existing stent grafts on new delivery devices and may require changing the delivery device system attachment site or increasing sheath compatibility size for the stent graft. Some solutions, such as retention systems including circumferentially asymmetric stent struts, may cause a bias in the radial force, and may infold under certain conditions. Stents that extend slightly beyond the edge of a graft material may pose problems including graft material folding, while not reducing material bulk enough to prevent modifications to the delivery system. The extension of stent structures beyond the edge of the graft material may interfere with blood flow into ancillary/branch vessels, and may cause access issues if additional procedures are required to treat the anatomy at a later time, thereby narrowing down treatment options, especially if conversion to open procedures is not possible or advisable.

Thus, there remains a need for further contributions in this area of technology.

SUMMARY

In one form of the present disclosure, a stent graft retention system for retaining a stent graft on a delivery device is provided. The stent graft retention system includes a stent graft including a first end, a second end, a first edge at the first end, and a stent including first apices and second apices, the first apices disposed adjacent the first end and the second apices extending toward the second end. The stent graft retention system further includes a plurality of discrete retention wire forms each including a first strut, a second strut, and an apex between the first and second struts. The first and second struts are attached to the stent graft a distance from the first edge and the apex extends beyond the first edge. The each discrete retention wire form is nested with an apex of the first apices. At least one of the plurality of discrete retention wire forms is configured to engage a trigger wire.

In another example of the present disclosure, a stent graft retention system for retaining a stent graft on a delivery device is provided. The stent graft retention system includes a stent graft including a first end, a second end, a first edge at the first end, and a stent comprising first apices and second apices, the first apices disposed adjacent the first end and the second apices extending toward the second end. The stent graft retention system further includes a plurality of discrete retention wire forms each including a first strut, a second strut, and an apex between the first and second struts. The first and second struts are attached to the stent graft a distance from the first edge and the apex extends beyond the first edge. The each discrete retention wire form is nested with an apex of the first apices. At least one of the plurality of discrete retention wire forms is configured to engage a trigger wire. The first and second struts of the each discrete retention wire form pass through eyelets in the stent graft and are attached to the stent graft on a first surface of the stent graft and the apex of the each discrete retention wire form extends beyond the first edge of a second surface of the stent graft, the second surface opposite the first surface.

In yet another example of the present disclosure, a stent graft retention system for retaining a stent graft on a delivery device is provided. The stent graft retention system includes a stent graft including a first end, a second end, a first edge at the first end, and a stent including first apices and second apices, the first apices disposed adjacent the first end and the second apices extending toward the second end. The stent graft retention system further includes a plurality of discrete retention wire forms each including a first loop, a second lop, and a wire attaching the first loop and the second loop. The first loop of the each discrete retention wire form is attached to the stent graft a distance from the first edge and the second loop extends beyond the first edge. The first loop of the each discrete retention wire form is attached to the stent graft between an apex of the first apices and the first edge. At least one of the plurality of discrete retention wire forms is configured to engage a trigger wire.

Further areas of applicability will become apparent from the description provided herein. It should be understood that the description and specific examples are intended for purposes of illustration only and are not intended to limit the scope of the present disclosure.

DRAWINGS

In order that the present disclosure may be well understood, there will now be described various forms thereof, given by way of example, reference being made to the accompanying drawings. The components in the figures are not necessarily to scale. Moreover, in the figures, like-referenced numerals designate corresponding parts throughout the different views.

Figure 6A:
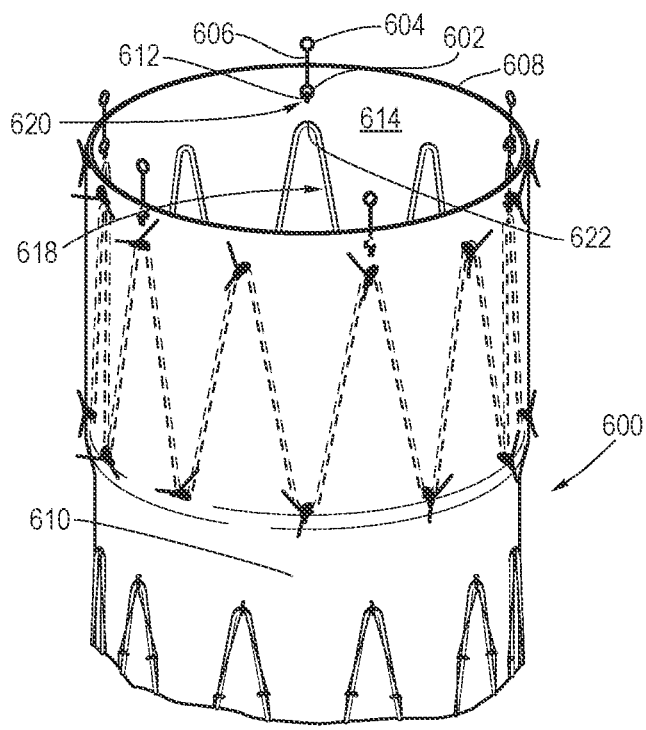
Figure 6B:
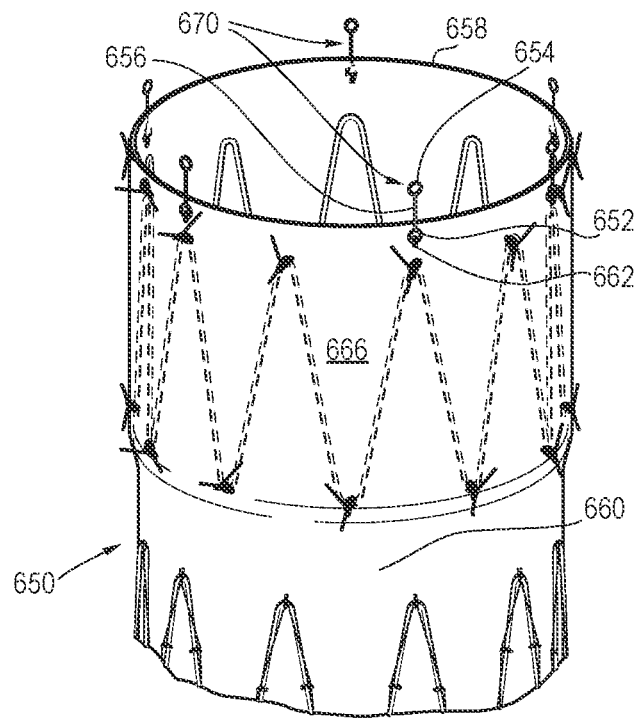
Figure 8A:
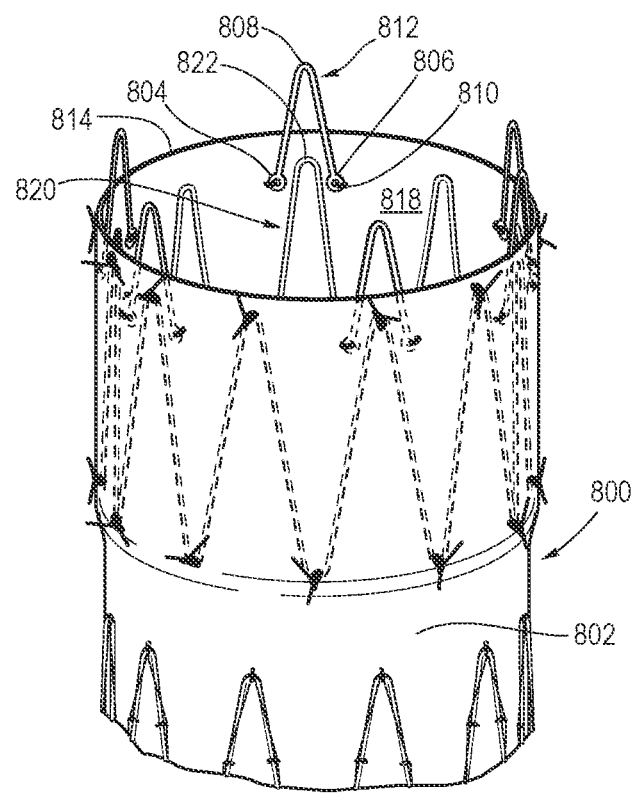
Figure 8B:
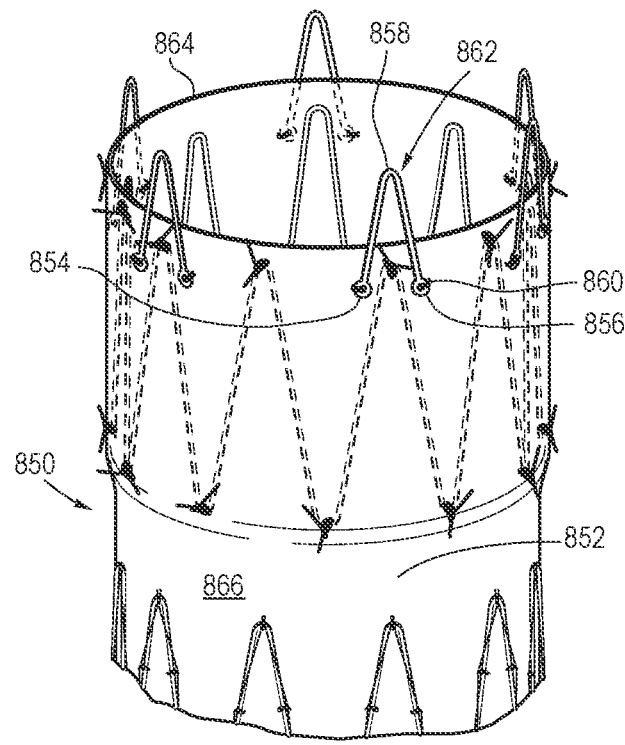
Figure 9A:
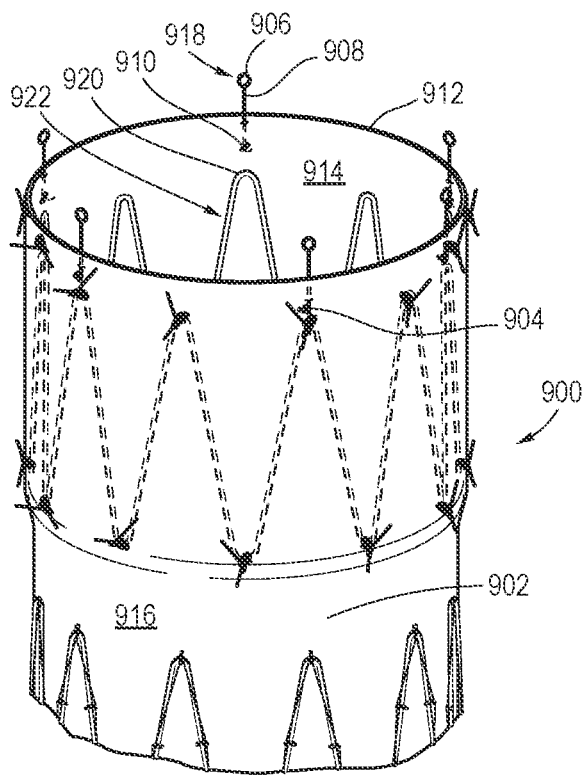
Figure 9B:
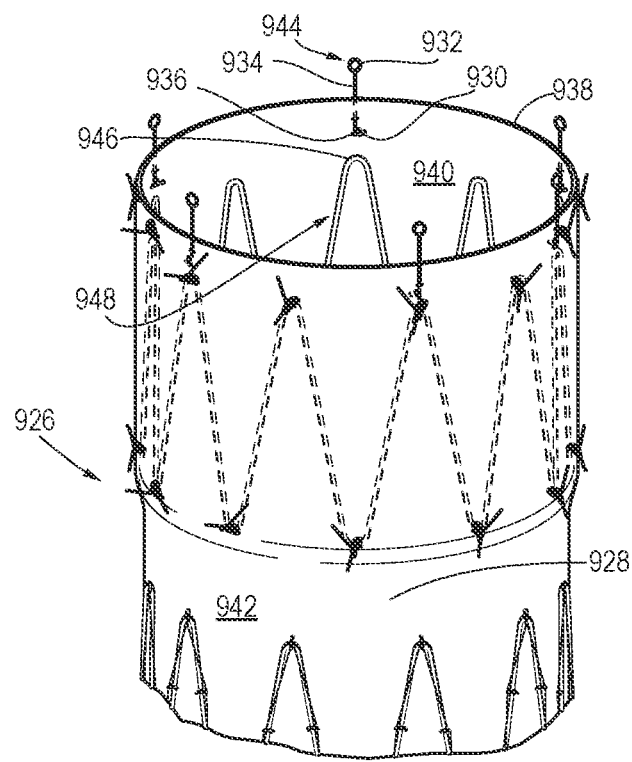
Figure 9C:
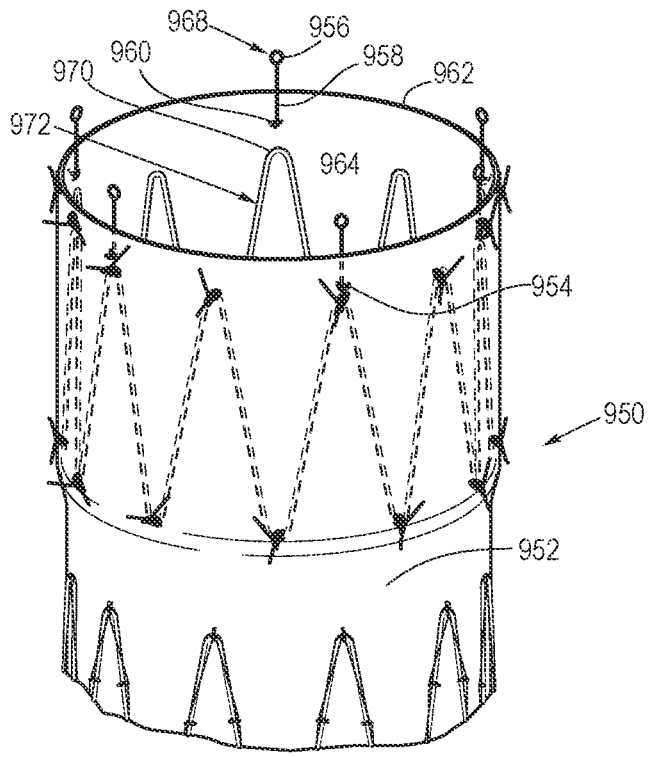
Figure 9D:
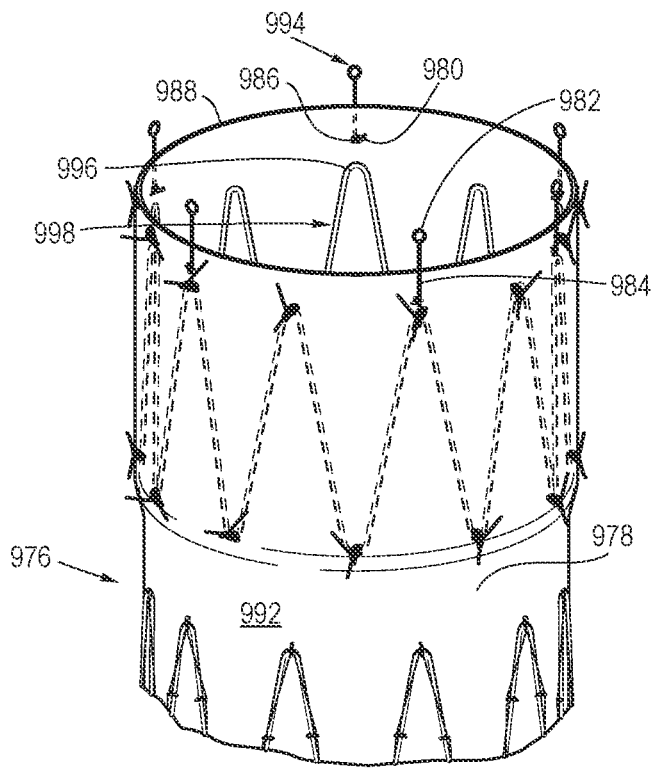
Figure 10A:
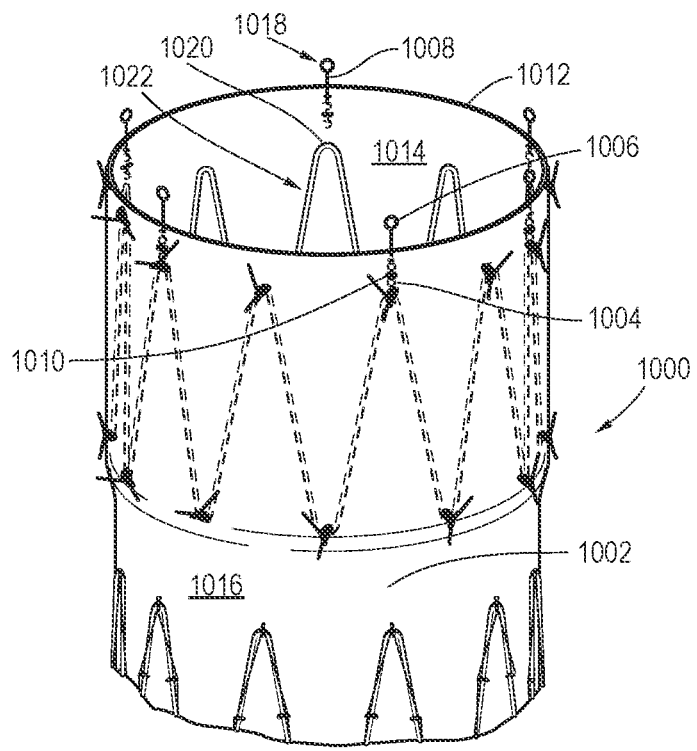
Figure 10B:
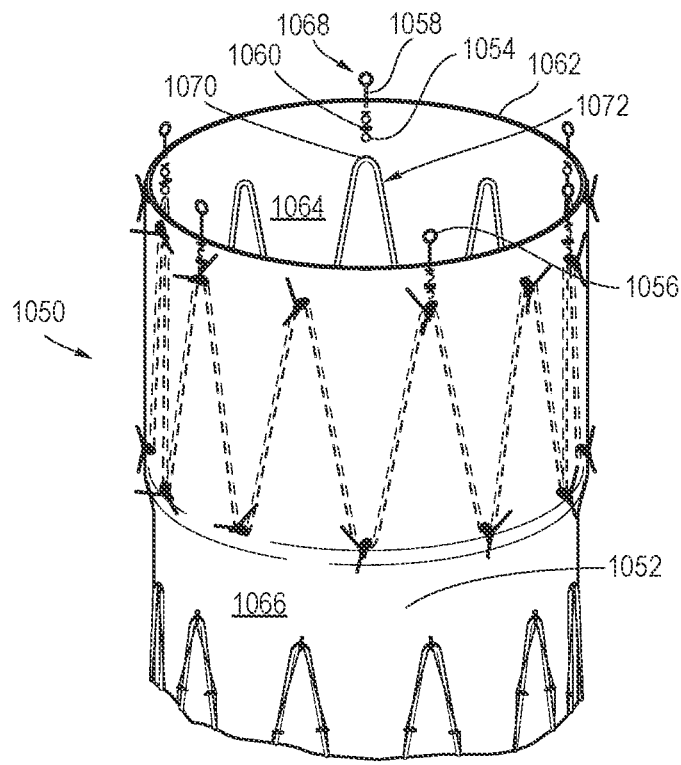
Figure 11A:
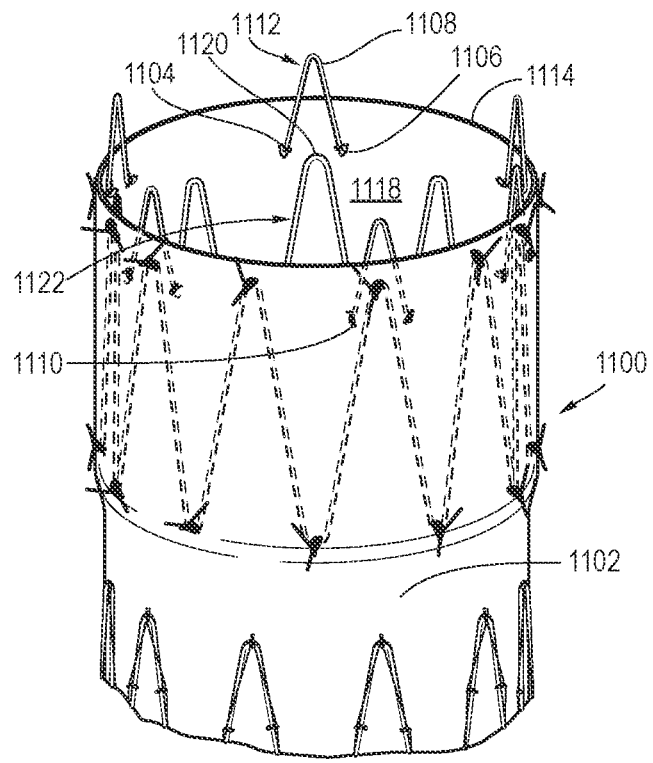
Figure 11B:
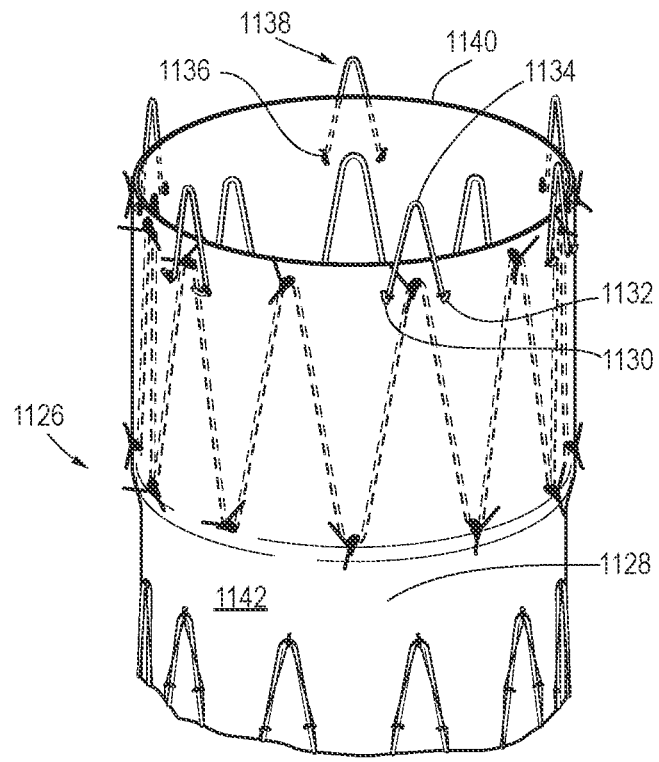
Figure 11C:
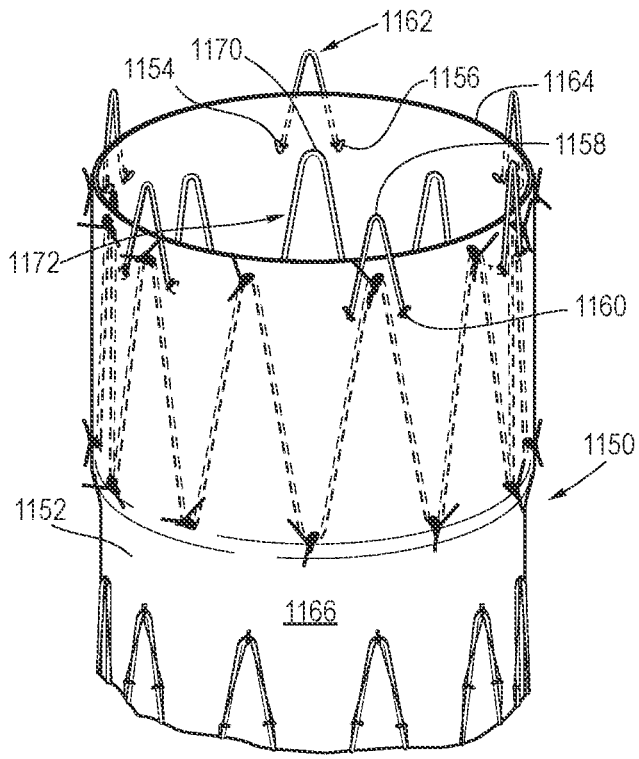
Figure 11D:
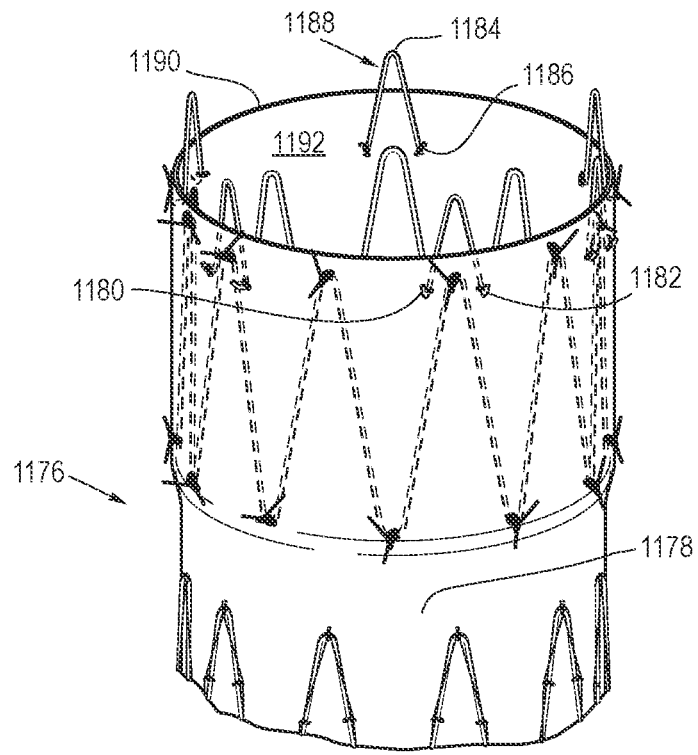
Figure 12:
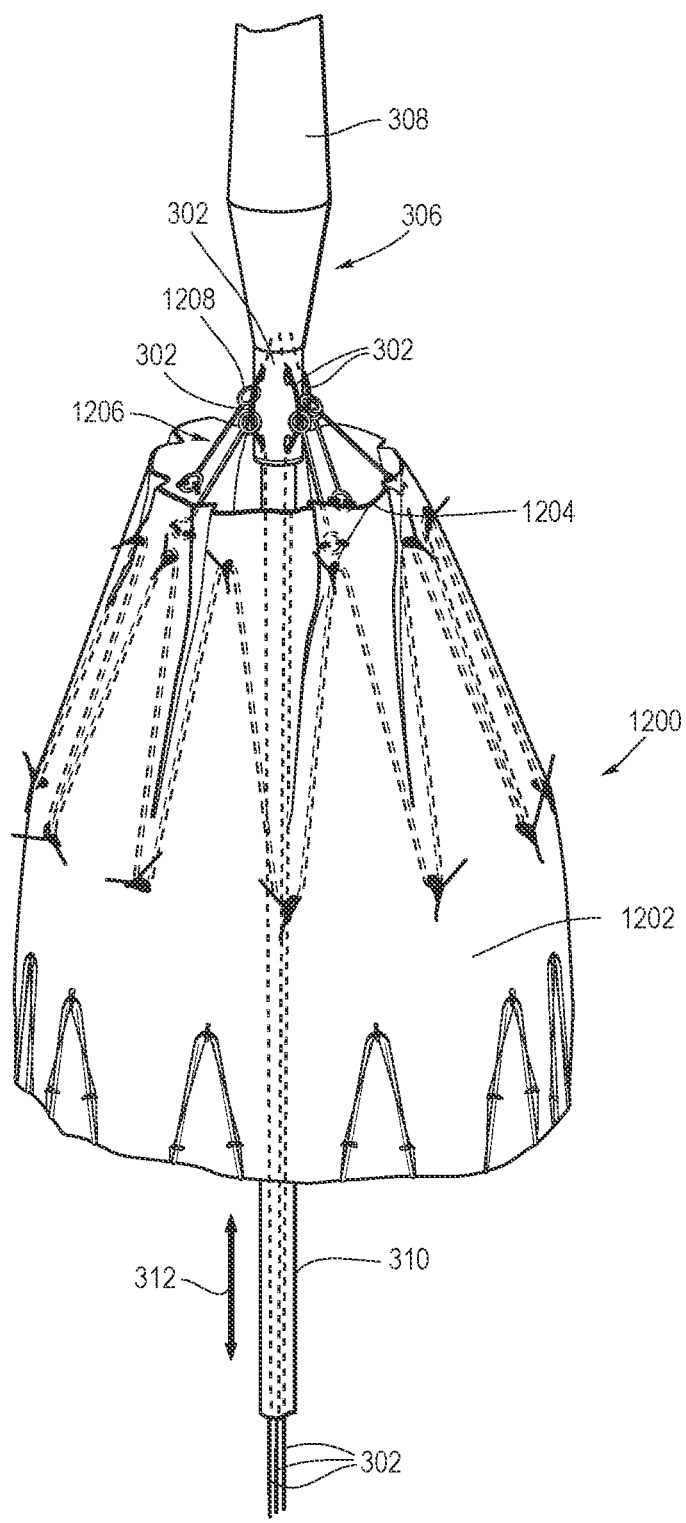
Figure 13A:
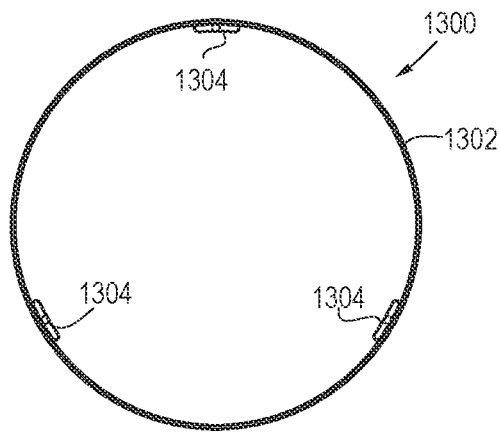
Figure 13B:
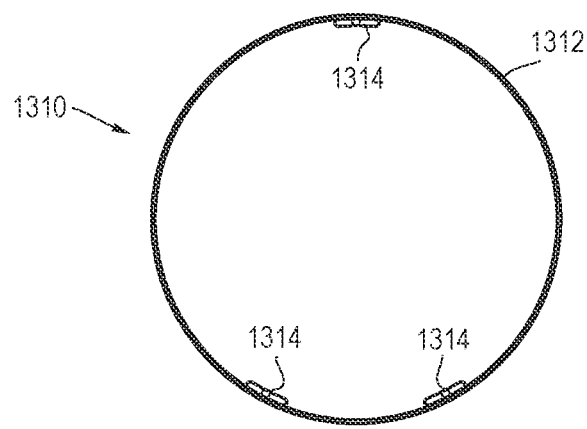
Figure 13C:
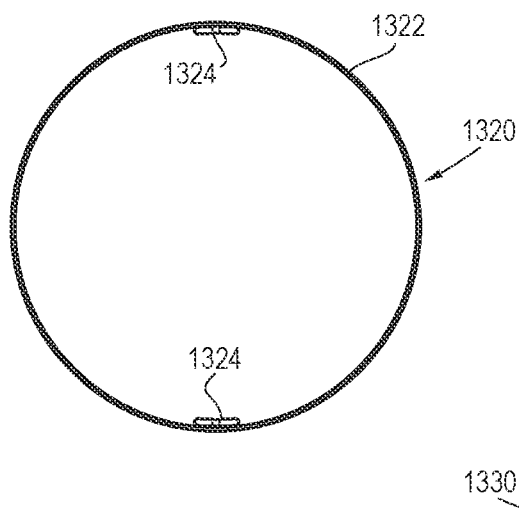
Figure 13D:
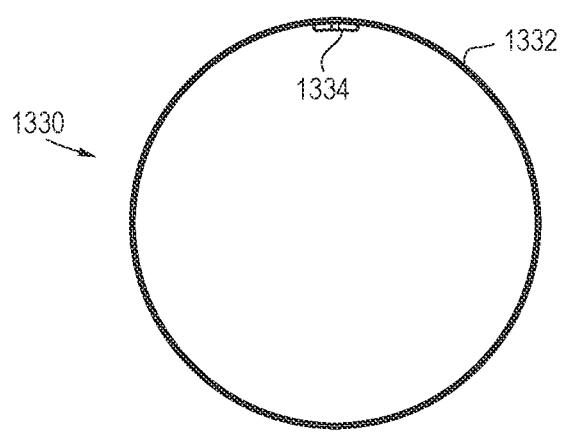
Figure 14:
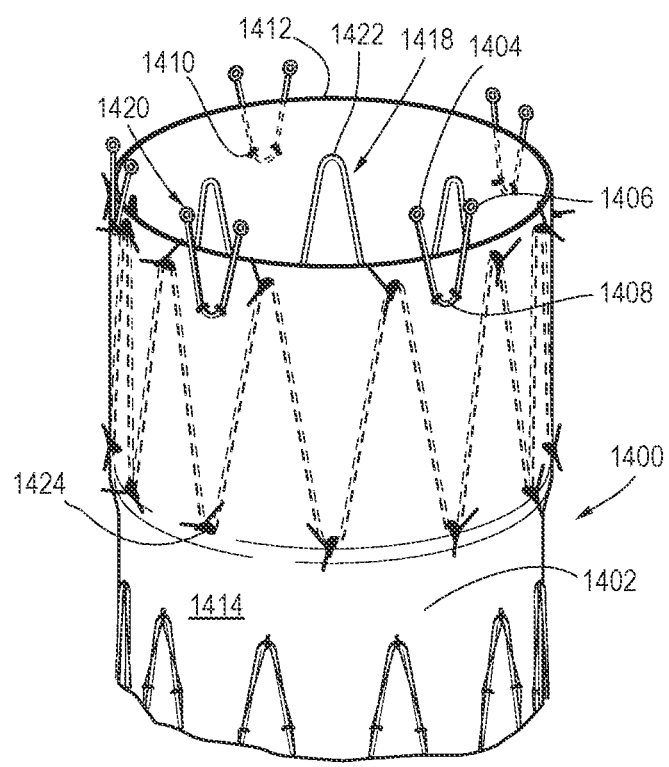
Figure 15A:
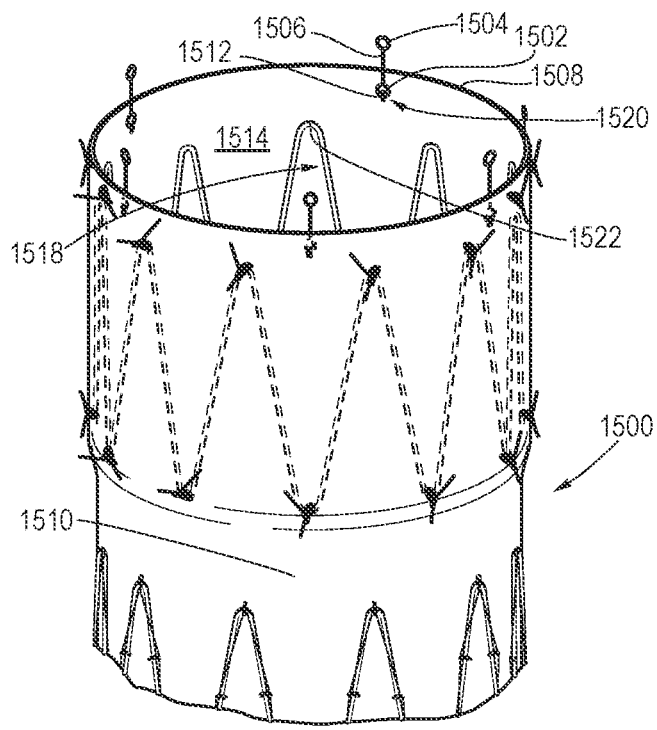
Figure 15B:
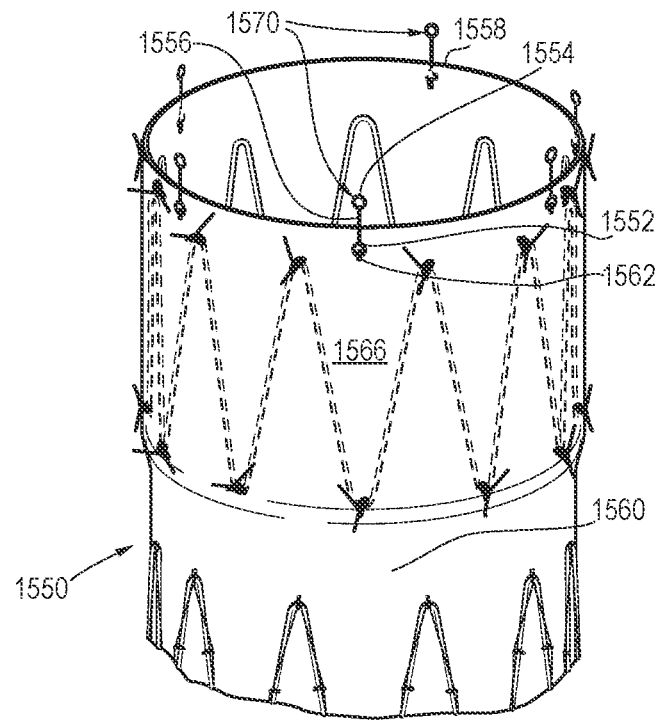
Figure 16A:
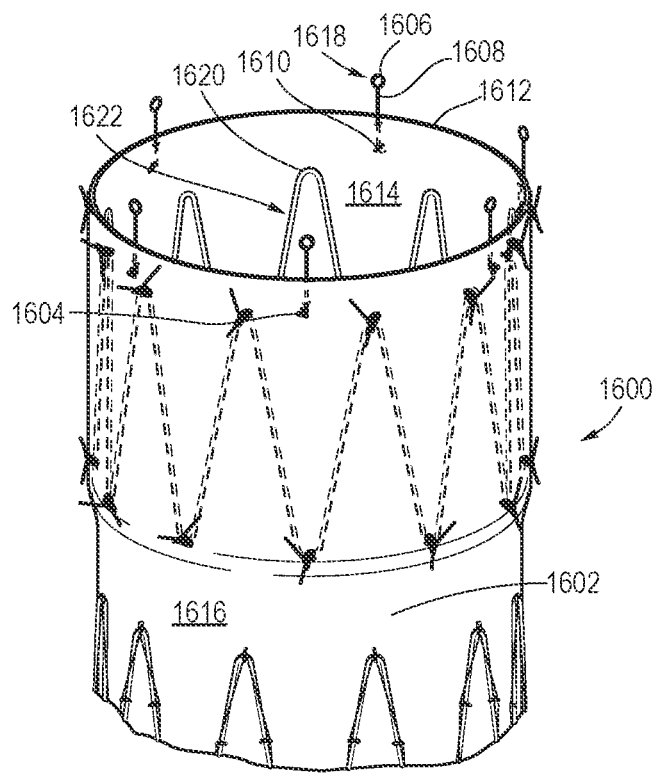
Figure 16B:
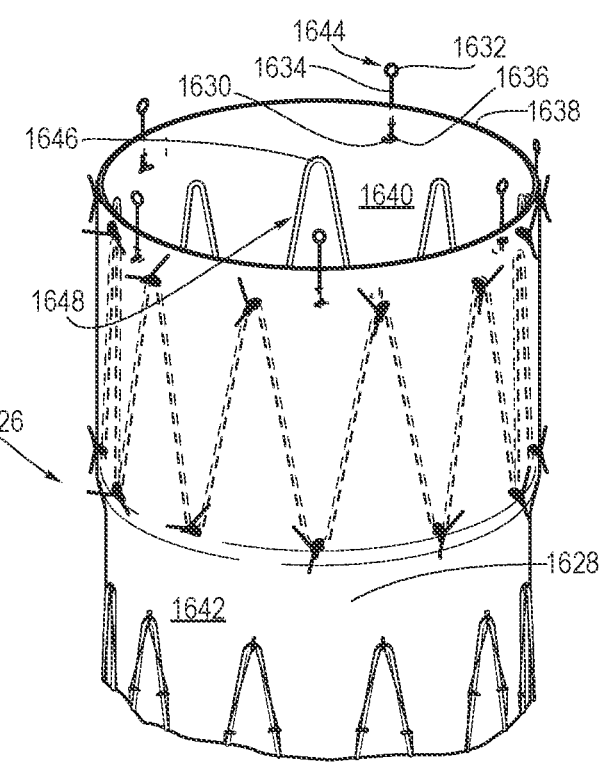
Figure 16C:
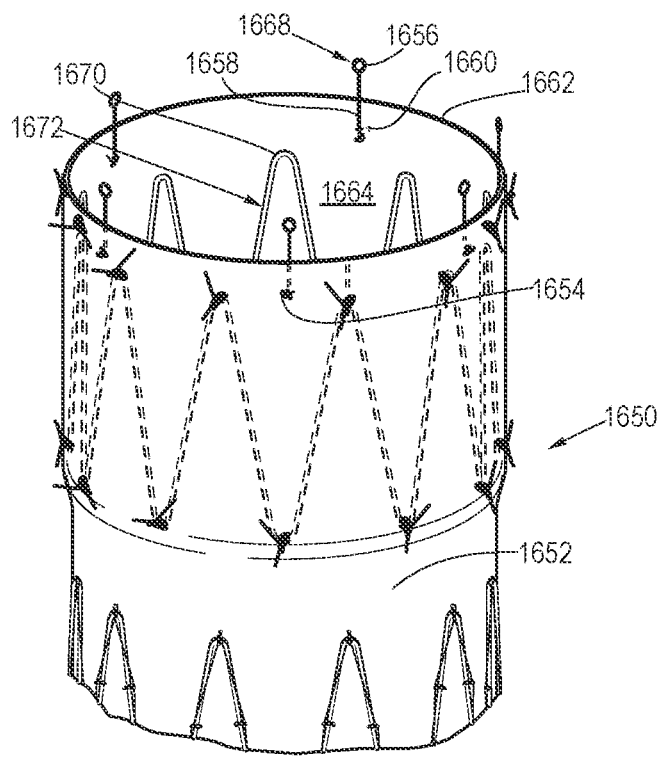
Figure 16D:
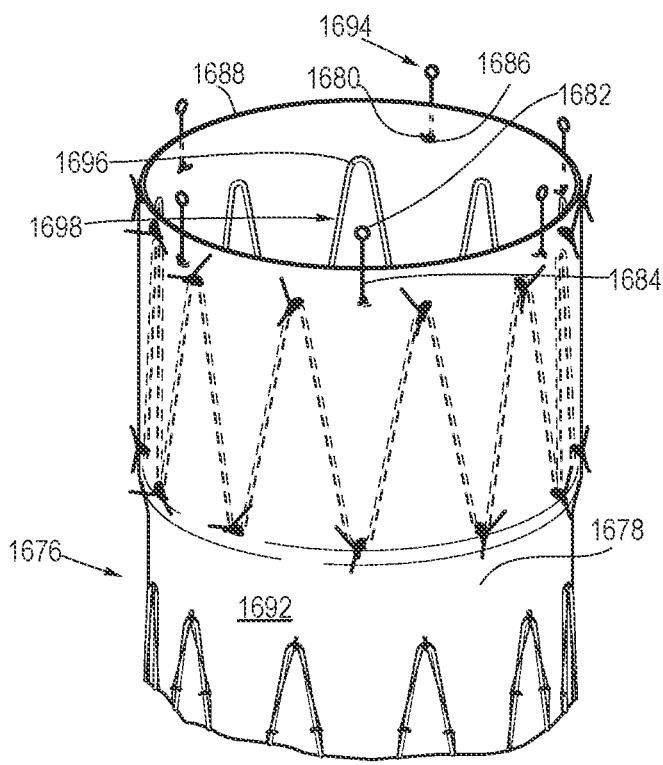
Figure 17A:
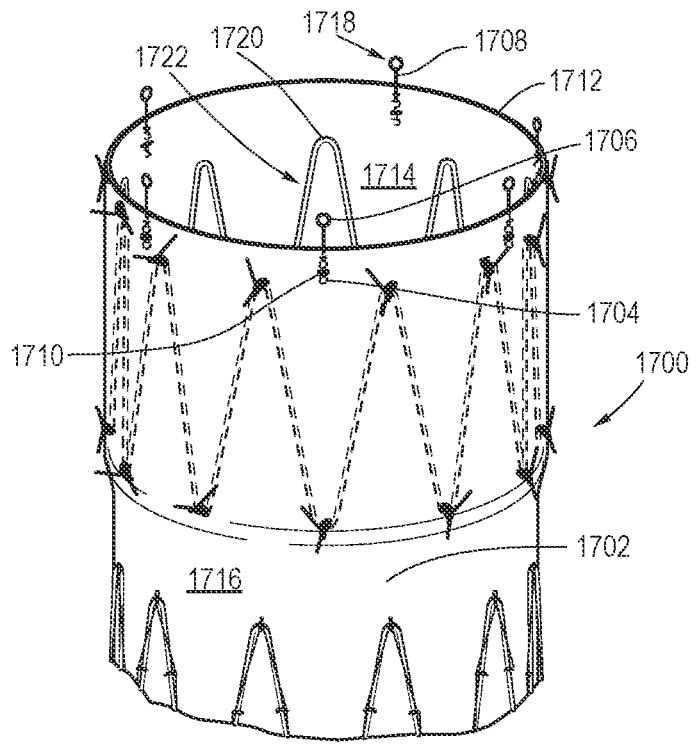
Figure 17B:
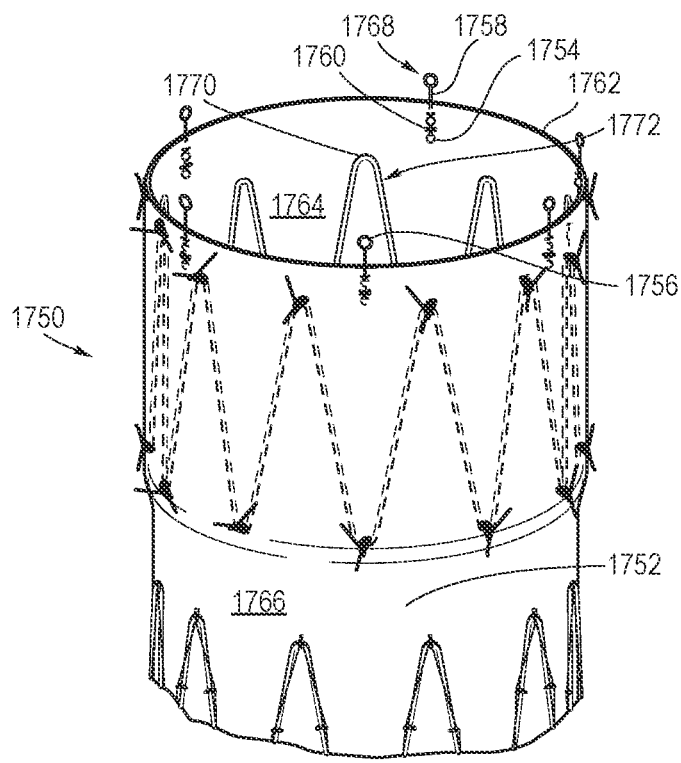

FIG. 6A illustrates an exploded partial perspective view of yet another example of a stent graft retention system including a plurality of discrete retention wire forms including first and second loops connected by a wire, the plurality of discrete retention wire forms disposed symmetrically about an inner surface of the stent graft, and attached to the stent graft at the first loop between a first apex of the stent and a first edge of the stent graft;

FIG. 6B illustrates an exploded partial perspective view of yet another example of a stent graft retention system including a plurality of discrete retention wire forms including first and second loops connected by a wire, the plurality of discrete retention wire forms disposed symmetrically about an outer surface of the stent graft, and attached to the stent graft at the first loop between a first apex of the stent and a first edge of the stent graft;

FIG. 7A illustrates an exploded partial perspective view of yet another example of a stent graft retention system including a stent graft including eyelets through which the first and second struts of the plurality of discrete retention wire forms pass, the first and second struts attached to an inner surface of the stent graft, and apices extending past the outer (i.e., opposite) surface of a first edge of the stent graft;

FIG. 7B illustrates an exploded partial perspective view of yet another example of a stent graft retention system including a stent graft including eyelets through which the first and second struts of the plurality of discrete retention wire forms pass, the first and second struts attached to an outer surface of the stent graft, and apices extending past the inner (i.e., opposite) surface of a first edge of the stent graft;

FIG. 8A illustrates an exploded partial perspective view of yet another example of a stent graft retention system including a plurality of discrete retention wire forms disposed symmetrically about an inner surface of a first edge of a stent graft, the each discrete retention wire form including first and second struts including loops;

FIG. 8B illustrates an exploded partial perspective view of yet another example of a stent graft retention system including a plurality of discrete retention wire forms disposed symmetrically about an outer surface of a first edge of a stent graft, the each discrete retention wire form including first and second struts including loops;

FIG. 9A illustrates an exploded partial perspective view of yet another example of a stent graft retention system including a plurality of discrete retention wire forms including a strut including a hook, and a loop, the hook and the loop connected by a wire, the plurality of discrete retention wire forms attached to an outer surface of the stent graft by the hook between a first apex of the stent and a first edge of the stent graft, the loop extending past the inner (i.e., opposite) surface of the first edge of the stent graft;

FIG. 9B illustrates an exploded partial perspective view of yet another example of a stent graft retention system including a plurality of discrete retention wire forms including a strut including a hook, and a loop, the hook and the loop connected by a wire, the plurality of discrete retention wire forms attached to an inner surface of the stent graft by the hook between a first apex of the stent and a first edge of the stent graft, the loop extending past the outer (i.e., opposite) surface of the first edge of the stent graft;

FIG. 9C illustrates an exploded partial perspective view of yet another example of a stent graft retention system including a plurality of discrete retention wire forms including a strut including a hook, and a loop, the hook and the loop connected by a wire, the plurality of discrete retention wire forms attached to an inner surface of the stent graft by the hook between a first apex of the stent and a first edge of the stent graft, the loop extending past the inner surface of the first edge of the stent graft;

FIG. 9D illustrates an exploded partial perspective view of yet another example of a stent graft retention system including a plurality of discrete retention wire forms including a strut including a hook, and a loop, the hook and the loop connected by a wire, the plurality of discrete retention wire forms attached to an outer surface of the stent graft by the hook between a first apex of the stent and a first edge of the stent graft, the loop extending past the outer surface of the first edge of the stent graft;

FIG. 10A illustrates an exploded partial perspective view of yet another example of a stent graft retention system including a plurality of discrete retention wire forms including a strut including a "bar-bell," and a loop, the bar-bell and the loop connected by a wire, the plurality of discrete retention wire forms attached to an outer surface of the stent graft by the bar-bell between a first apex of the stent and a first edge of the stent graft, the loop extending past the inner (i.e., opposite) surface of a first edge of the stent graft;

FIG. 10B illustrates an exploded partial perspective view of yet another example of a stent graft retention system including a plurality of discrete retention wire forms including a strut including a "bar-bell," and a loop, the bar-bell and the loop connected by a wire, the plurality of discrete retention wire forms attached to an inner surface of the stent graft by the bar-bell between a first apex of the stent and a first edge of the stent graft, the loop extending past the outer (i.e., opposite) surface of the first edge of the stent graft;

FIG. 11A illustrates an exploded partial perspective view of yet another example of a stent graft retention system including a plurality of discrete retention wire forms disposed symmetrically about an inner surface of a first edge of a stent graft, each discrete retention wire form including first and second struts including hooks extending inward from the inner surface of the stent graft;

FIG. 11B illustrates an exploded partial perspective view of yet another example of a stent graft retention system including a plurality of discrete retention wire forms disposed symmetrically about an outer surface of a first edge of a stent graft, each discrete retention wire form including first and second struts including hooks extending outward from the outer surface of the stent graft;

FIG. 11C illustrates an exploded partial perspective view of yet another example of a stent graft retention system including a plurality of discrete retention wire forms disposed symmetrically about an outer surface of a first edge of a stent graft, each discrete retention wire form including first and second struts including hooks extending inward through the stent graft;

FIG. 11D illustrates an exploded partial perspective view of yet another example of a stent graft retention system including a plurality of discrete retention wire forms disposed symmetrically about an inner surface of a first edge of a stent graft, each discrete retention wire form including first and second struts including hooks extending outward through the stent graft;

FIG. 12 illustrates an exploded partial perspective view of yet another example of a stent graft retention system, in which trigger wires of an example of a delivery device have engaged the plurality of discrete retention wire forms including first and second loops connected by a wire, the trigger wires engaging the second loop of the each discrete retention wire form, resulting in closing of the first edge of the stent graft;

FIG. 13A illustrates a longitudinal end view of yet another example of a stent graft retention system, in which three discrete retention wire forms are disposed evenly about the circumference of the inner surface of the stent graft;

FIG. 13B illustrates a longitudinal end view of yet another example of a stent graft retention system, in which three discrete retention wire forms are disposed unevenly about the circumference of the inner surface of the stent graft;

FIG. 13C illustrates a longitudinal end view of yet another example of a stent graft retention system in which two discrete retention wire forms are disposed evenly about the circumference of the inner surface of the stent graft;

FIG. 13D illustrates a longitudinal end view of yet another example of a stent graft retention system in which a discrete retention wire form is attached to the inner surface of the stent graft;

FIG. 14 illustrates an exploded partial perspective view of yet another example of a stent graft retention system including a plurality of discrete retention wire forms disposed symmetrically about an outer surface of a first edge of a stent graft, the each discrete retention wire form including first and second struts including loops, the first and second struts extending past the first edge of the stent graft;

FIG. 15A illustrates an exploded partial perspective view of yet another example of a stent graft retention system including a plurality of discrete retention wire forms including first and second loops connected by a wire, the plurality of discrete retention wire forms disposed symmetrically about an inner surface of the stent graft, and attached to the stent graft at the first loop between two apices of first apices of the stent;

FIG. 15B illustrates an exploded partial perspective view of yet another example of a stent graft retention system including a plurality of discrete retention wire forms including first and second loops connected by a wire, the plurality of discrete retention wire forms disposed symmetrically about an outer surface of the stent graft, and attached to the stent graft at the first loop between two apices of first apices of the stent;

FIG. 16A illustrates an exploded partial perspective view of yet another example of a stent graft retention system including a plurality of discrete retention wire forms including a strut including a hook, and a loop, the hook and the loop connected by a wire, the plurality of discrete retention wire forms attached to an outer surface of the stent graft by the hook between two apices of first apices of the stent, the loop extending past the inner (i.e., opposite) surface of a first edge of the stent graft;

FIG. 16B illustrates an exploded partial perspective view of yet another example of a stent graft retention system including a plurality of discrete retention wire forms including a strut including a hook, and a loop, the hook and the loop connected by a wire, the plurality of discrete retention wire forms attached to an inner surface of the stent graft by the hook between two apices of first apices of the stent, the loop extending past the outer (i.e., opposite) surface of a first edge of the stent graft;

FIG. 16C illustrates an exploded partial perspective view of yet another example of a stent graft retention system including a plurality of discrete retention wire forms including a strut including a hook, and a loop, the hook and the loop connected by a wire, the plurality of discrete retention wire forms attached to an inner surface of the stent graft by the hook between two apices of first apices of the stent, the loop extending past the inner surface of a first edge of the stent graft;

FIG. 16D illustrates an exploded partial perspective view of yet another example of a stent graft retention system including a plurality of discrete retention wire forms including a strut including a hook, and a loop, the hook and the loop connected by a wire, the plurality of discrete retention wire forms attached to an outer surface of the stent graft by the hook between two apices of first apices of the stent, the loop extending past the outer surface of a first edge of the stent graft;

FIG. 17A illustrates an exploded partial perspective view of yet another example of a stent graft retention system including a plurality of discrete retention wire forms including a strut including a "bar-bell," and a loop, the bar-bell and the loop connected by a wire, the plurality of discrete retention wire forms attached to an outer surface of the stent graft by the bar-bell between two apices of the first apices of the stent, the loop extending past the inner (i.e., opposite) surface of a first edge of the stent graft; and FIG. 17B illustrates an exploded partial perspective view of yet another example of a stent graft retention system including a plurality of discrete retention wire forms including a strut including a "bar-bell," and a loop, the bar-bell and the loop connected by a wire, the plurality of discrete retention wire forms attached to an inner surface of the stent graft by the bar-bell between two apices of the first apices of the stent, the loop extending past the outer (i.e., opposite) surface of a first edge of the stent graft.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

In adding reference denotations to elements of each drawing, although the same elements are displayed on a different drawing, it should be noted that the same elements have the same denotations. In addition, in describing one aspect of the present disclosure, if it is determined that a detailed description of related well-known configurations or functions blurs the gist of one aspect of the present disclosure, it will be omitted.

In the following discussion, the terms "first" and "second" will be used to describe the opposing axial ends of the stent grafts of the present disclosure, toward which the first and second apices of a stent extend, as well as the axial ends of various component features. The term "longitudinal" will be used to refer to an axis that aligns with the first-second axis of the device (or component). The terms "radially" and "radial" will be used to refer to elements, surfaces, or assemblies relative to one another that may extend perpendicularly from a longitudinal axis. The terms "circumference," "circumferentially," and "circumferential" will be used to refer to elements, surfaces, or assemblies relative to one another encircling a longitudinal axis at a radius.

The uses of the terms "a" and "an" and "the" and similar referents in the context of describing the present disclosure (especially in the context of the following claims) are to be construed to cover both the singular and the plural, unless otherwise indicated herein or clearly contradicted by context. The use of the term "plurality of" is defined by the Applicant in the broadest sense, superseding any other implied definitions or limitations hereinbefore or hereinafter unless expressly asserted by the Applicant to the contrary, to mean a quantity of more than one. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

As used herein the terms "comprise(s)," "include(s)," "having," "has," "can," "contain(s)," and variants thereof, are intended to be open-ended transitional phrases, terms, or words that do not preclude the possibility of additional acts or structures. The present description also contemplates other embodiments "comprising," "consisting of," and "consisting essentially of," the examples or elements presented herein, whether explicitly set forth or not.

In describing elements of the present disclosure, the terms $1^{st}$, $2^{nd}$, first, second, A, B, (a), (b), and the like, may be used herein. These terms are only used to distinguish one element from another element, but do not limit the corresponding elements irrespective of the nature or order of the corresponding elements.

Unless otherwise defined, all terms used herein, including technical or scientific terms, have the same meanings as those generally understood by those skilled in the art to which the present disclosure pertains. Such terms as those defined in a generally used dictionary are to be interpreted as having meanings equal to the contextual meanings in the relevant field of art.

Figure 1:
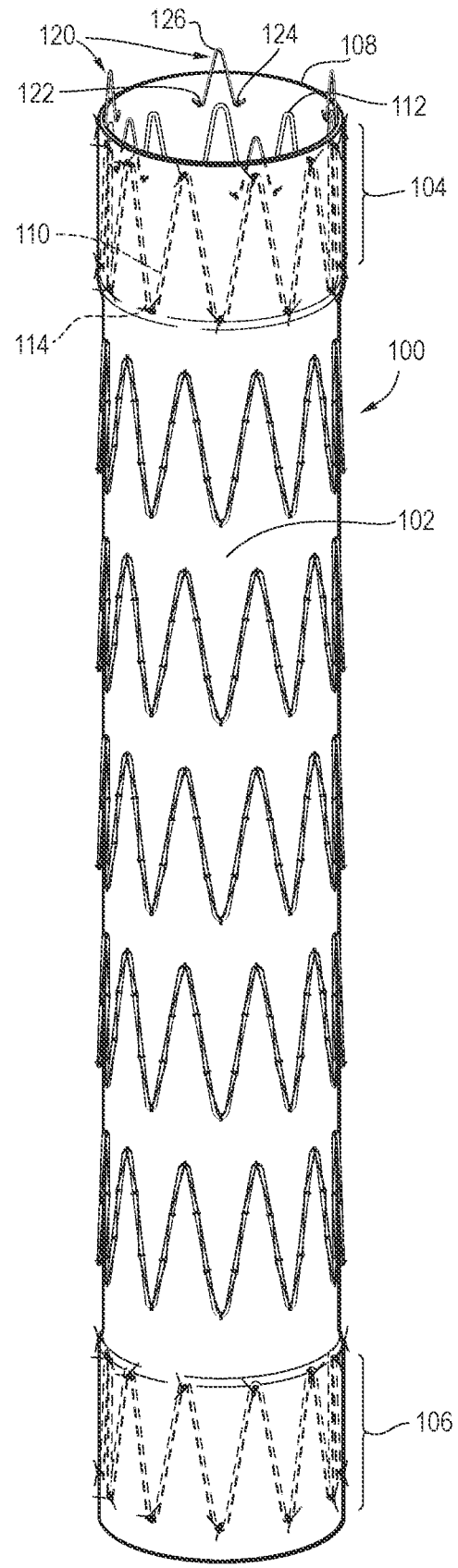
FIG. 1 illustrates a perspective view of an example of a stent graft retention system according to the principles of the present disclosure.

Referring to FIG. 1, an example of a stent graft retention system 100 is illustrated. Stent graft retention system 100 includes stent graft 102 and retains stent graft 102 on a delivery device, such as a trigger wire. Stent graft 102 includes first end 104, second end 106, first edge 108 at first end 104, and a stent 110 including first apices 112 and second apices 114. First apices 112 may be disposed adjacent first end 104 and second apices 114 may extend toward second end 106. Stent graft retention system 100 further includes a plurality of discrete retention wire forms 120. Each discrete retention wire form 120 includes first strut 122, second strut 124, and apex 126. First and second struts 122, 124 of the each discrete retention wire form 120 are attached to stent graft 102 a distance from first edge 108 such that apex 126 extends beyond first edge 108. As shown in FIG. 1, apex 126 of the each discrete retention wire form 120 and apex 112 of the first apices 112 may be coaxial and first and second struts 122, 124 are attached to stent graft 102 on opposite sides, circumferentially, of an apex 112 of the first apices 112. Alternatively, though not shown in FIG. 1, apex 126 of the each discrete retention wire form 120 may be positioned circumferentially between two apices 112 of the first apices 112. The each discrete retention wire form 120 may be "v-shaped," with the "bottom" of the "v-shape" corresponding to apex 126 and the "top" of the "v-shape" corresponding to first and second struts 122, 124. Apex 126 may not necessarily be in the form of a sharp tip. Rather, first and second struts 122, 124 may extend away from apex 126 in a non-parallel fashion. The plurality of discrete retention wire forms 120 is attached to stent graft 102 such that the plurality of discrete retention wire forms 120 are evenly and symmetrically distributed about a circumference of stent graft 102. In some examples not shown, the plurality of discrete retention wire forms 120 are unevenly and asymmetrically distributed about a circumference of stent graft 102.

The stent 110 may be made from numerous metals and alloys. In one example, stent 110 includes a shape-memory material such as a nickel-titanium alloy ("nitinol"). Stent 110 may include materials such as stainless steel, MP35N, gold, tantalum, platinum or platinum iridium, platinum chromium, platinum iron, niobium, tungsten, inconel, ceramic, nickel, titanium, stainless steel/titanium composite, cobalt, chromium, cobalt/chromium alloys, magnesium, aluminum, or other biocompatible or bioresorbable metallic materials and/or composites or alloys. Examples of other materials that may be used to form stent 110 include carbon or carbon fiber; cellulose acetate, cellulose nitrate, silicone, polyethylene terephthalate, polyurethane, polyamide, polyester, polyorthoester, polyanhydride, polyether sulfone, polycarbonate, polypropylene, ultra-high molecular weight polyethylene, polytetrafluoroethylene, or another biocompatible polymeric material, or mixtures or copolymers of these; polylactic acid, polyglycolic acid, or copolymers thereof: a polyanhydride, polycaprolactone, polyhydroxybutyrate valerate, or another biodegradable polymer, or mixtures or copolymers of these; a protein, an extracellular matrix component, collagen, fibrin, or another biologic agent; or a suitable mixture thereof.

Moreover, the structure of stent 110 may be formed in a variety of ways to provide a suitable intraluminal support structure. The at least one stent 110 may be configured in the form of one or more "Z-stents" or Gianturco stents, each of which may comprise a series of substantially straight segments interconnected by a series of bent segments. The bent segments may include acute bends or apices, such as first apices 112 and second apices 114. The Gianturco stents are arranged in a zigzag configuration in which the straight segments are set at angles relative to each other and are connected by first apices 112 and second apices 114. The at least one stent 110 may be configured as a spiralized Z-stent.

Stent graft 102 may comprise a polymeric sheet having any suitable porosity. The porosity may be substantially porous or substantially non-porous and may be selected depending on the application. In one example, a porous polymeric sheet may comprise the polyurethane Thoralon®. In addition to, or in lieu of, a porous polyurethane, stent graft 102 may include any biocompatible polymeric material including non-porous polyurethanes, PTFE, expanded PTFE (ePTFE), polyethylene tetraphthalate ("PET"), aliphatic polyoxaesters, polylactides, polycaprolactones, and hydrogels.

The each discrete retention wire form may be in a "nested" relationship with an apex of the first apices of a stent. One or more of the apices of the first apices of a stent may be disposed coincident with or proximally beyond the distal ends (within the valley) of a v-shaped discrete retention wire form. In the case of a straight discrete retention wire form, the distal end of the straight discrete retention wire form may be disposed between two apices of the first apices of a stent such that the distal end is disposed coincident with or extends distally beyond the two apices of the first apices of the stent. In other words, the distal end of the straight discrete retention wire form extends to or into a valley between two apices of the first apices of the stent.

The term "biocompatible," as used here, unless stated otherwise, alone or in combination with other terms, refers to a material that is substantially non-toxic in the in vivo environment of its intended use, and that is not substantially rejected by the patient's physiological system. A biocompatible structure or material, when introduced into a majority of patients, will not cause an undesirably adverse, long-lived, or escalating biological reaction or response. Such a response is distinguished from a mild, transient inflammation that typically accompanies surgery or implantation of foreign objects into a living organism.

Figure 2A:
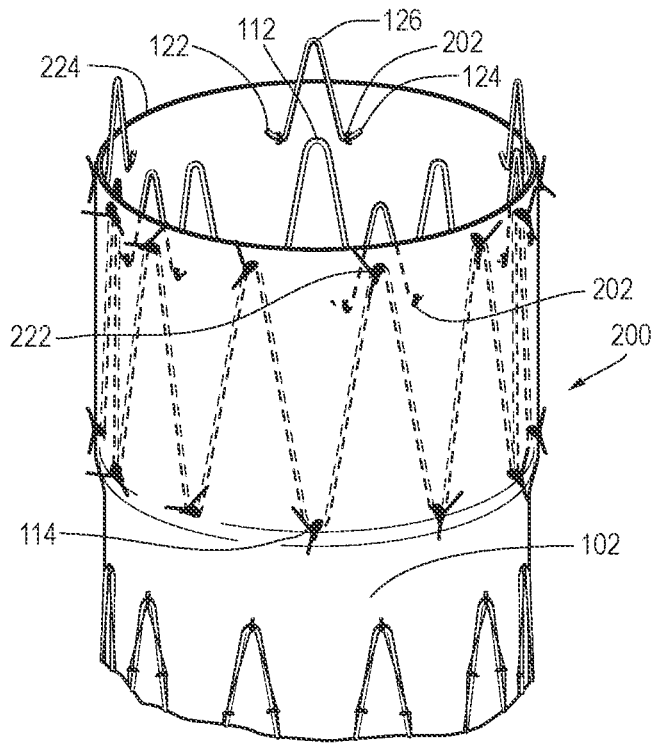
FIG. 2A illustrates an exploded partial perspective view of an example of a stent graft retention system including a plurality of discrete retention wire forms disposed symmetrically about an inner surface of a first edge of a stent graft, the each discrete retention wire form including first and second struts including flat hooks.

Referring to FIG. 2A, an exploded partial perspective view of an example of a stent graft retention system 200 is illustrated. Stent graft retention system 200 includes a plurality of discrete retention wire forms 120 attached to an inner surface of stent graft 102 by sutures 202 at first and second struts 122, 124. As shown in FIG. 2A, first and second struts 122, 124 of the each discrete retention wire form 120 include flat hooks. First and second struts 122, 124 of the discrete retention wire form 120 nested with apex 112 are positioned closer to first edge 224 of stent graft 102 than first and second struts 122, 124 of the discrete retention wire form 120 nested with apex 222. First and second struts 122, 124 of the each discrete retention wire form 120 may be independently positioned between stent 110 and first edge 224 of stent graft 102 relative to each of the other the each discrete retention wire form 120, or the plurality of discrete retention wire forms 120 may be positioned identically between stent 110 and first edge 224 of stent graft 102.

Figure 2B:
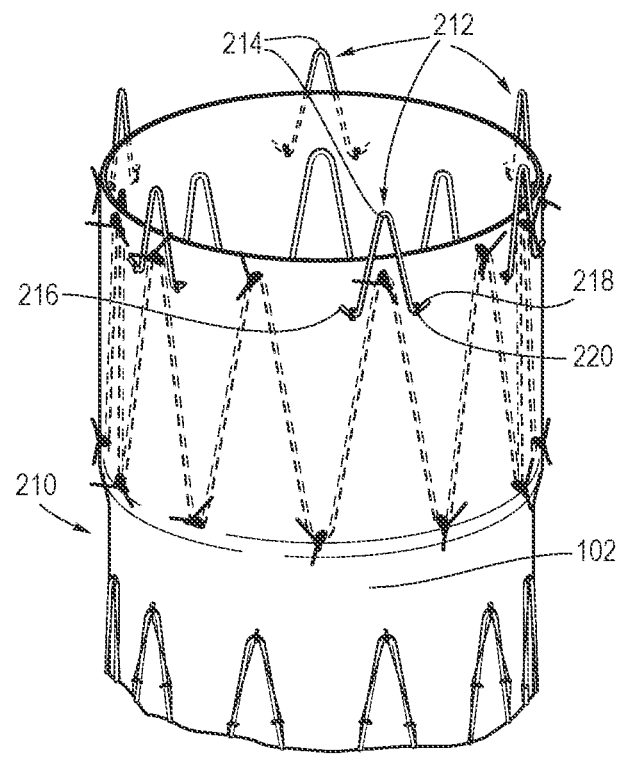
FIG. 2B illustrates an exploded partial perspective view of another example of a stent graft retention system including a plurality of discrete retention wire forms disposed symmetrically about an outer surface of a first edge of a stent graft.

Referring to FIG. 2B, an exploded partial perspective view of another example of a stent graft retention system 210 is illustrated. Stent graft retention system 210 includes a plurality of discrete retention wire forms 212 attached to an outer surface of stent graft 102 by sutures 220 at first and second struts 216, 218.

Figure 3:
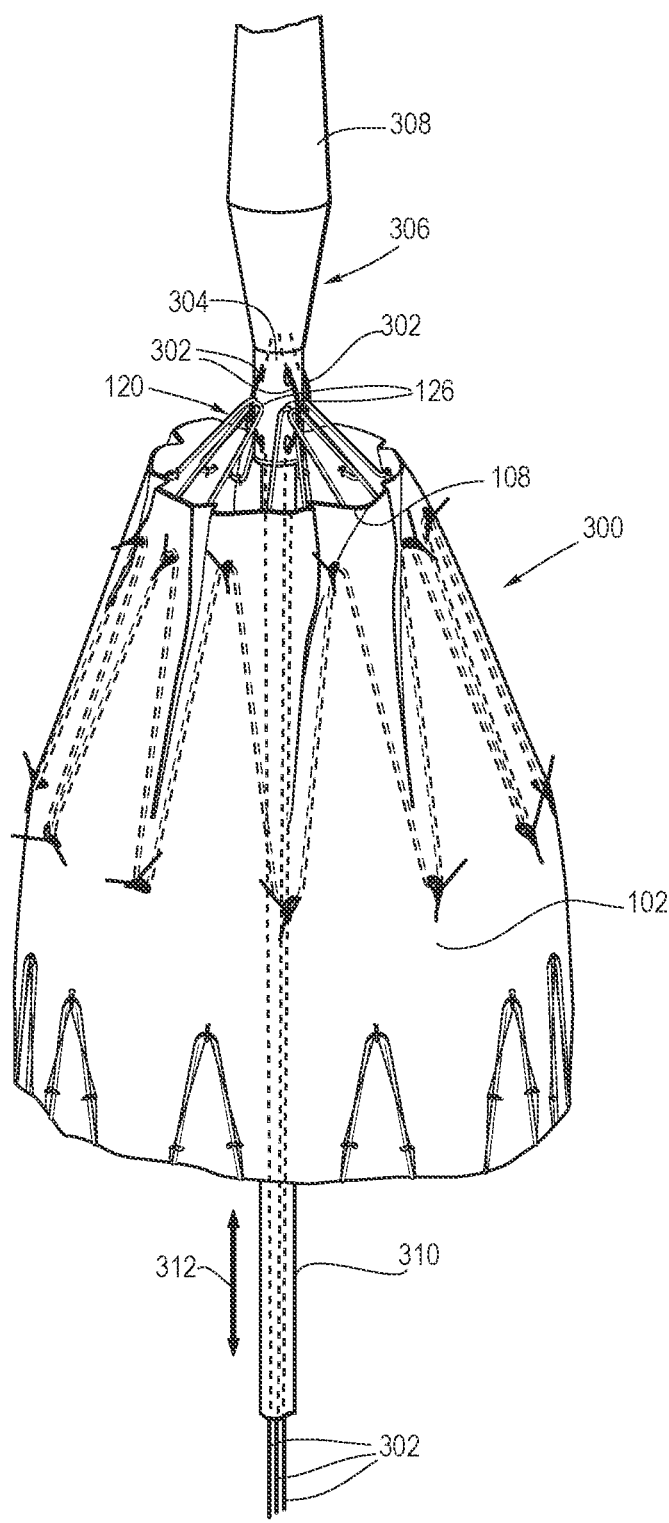
FIG. 3 illustrates an exploded partial perspective view of yet another example of a stent graft retention system, in which trigger wires of an example of a delivery device have engaged the plurality of discrete retention wire forms resulting in closing of the first edge of the stent graft.

Referring to FIG. 3, an exploded partial perspective view of yet another example of a stent graft retention system 300 is illustrated. Stent graft retention system 300 includes stent graft 102. As shown in FIG. 3, at least one of the plurality of discrete retention wire forms 120 engages trigger wires 302 of delivery device 306. Trigger wires 302 confront apex 126 of each discrete retention wire form 120 on the side of each discrete retention wire form 120 toward second end 106. Trigger wires 302 each run out of one hole in nose cone 304 of delivery device 306 and into another hole. Nose cone 304 is connected to body 308 of delivery device 306. Trigger wires 302 continue into cannula 310 that passes through the center of stent 110 and stent graft 102 parallel to a center longitudinal axis 312 of stent graft 102. When trigger wires 302 of delivery device 306 engage the plurality of discrete retention wire forms 120 at apex 126, first edge 108 of stent graft 102 may close toward the center longitudinal axis 312.

Figure 4A:
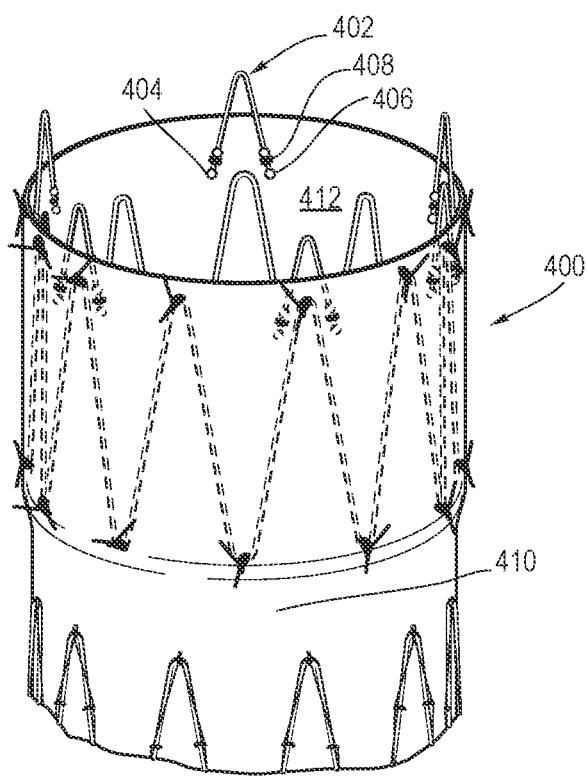
FIG. 4A illustrates an exploded partial perspective view of yet another example of a stent graft retention system including a plurality of discrete retention wire forms disposed symmetrically about an inner surface of a first edge of a stent graft, the each discrete retention wire form including first and second struts including "bar-bells"

Referring to FIG. 4A, an exploded partial perspective view of yet another example of a stent graft retention system 400 is illustrated. Stent graft retention system 400 includes a plurality of discrete retention wire forms 402 attached to an inner surface 412 of stent graft 410 by sutures 408 at first and second struts 404, 406. As shown in FIG. 4A, first and second struts 404, 406 of the each discrete retention wire form 402 include "bar-bell" shapes. Sutures 408 are configured to attach first and second struts 404, 406 to stent graft 410 around a "bar" of each "bar-bell" shape.

Figure 4B:
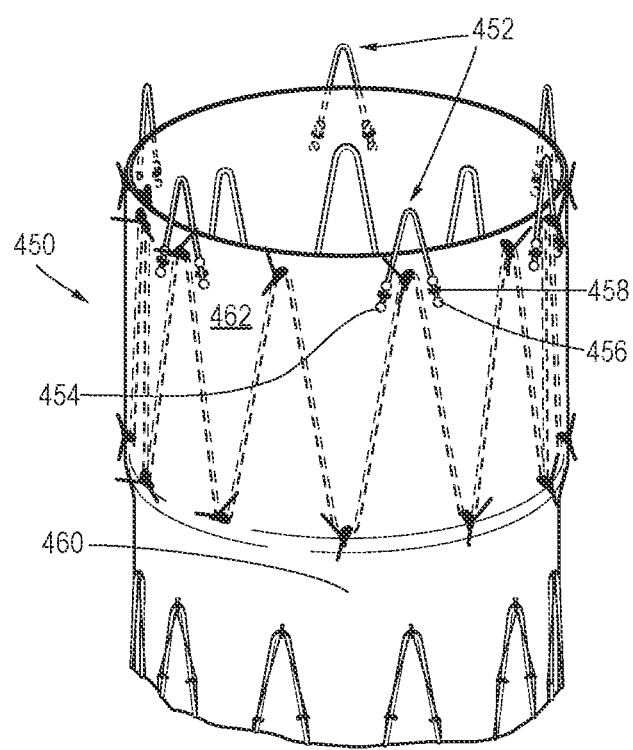
FIG. 4B illustrates an exploded partial perspective view of yet another example of a stent graft retention system including a plurality of discrete retention wire forms disposed symmetrically about an outer surface of a first edge of a stent graft, the each discrete retention wire form including first and second struts including "bar-bells"

Referring to FIG. 4B, an exploded partial perspective view of yet another example of a stent graft retention system 450 is illustrated. Stent graft retention system 450 includes a plurality of discrete retention wire forms 452 attached to an outer surface 462 of stent graft 460 by sutures 458 at first and second struts 454, 456. As shown in FIG. 4B, first and second struts 454, 456 of the each discrete retention wire form 452 include "bar-bell" shapes. Sutures 458 are configured to attach first and second struts 454, 456 to stent graft 460 around a "bar" of each "bar-bell" shape.

Figure 5A:
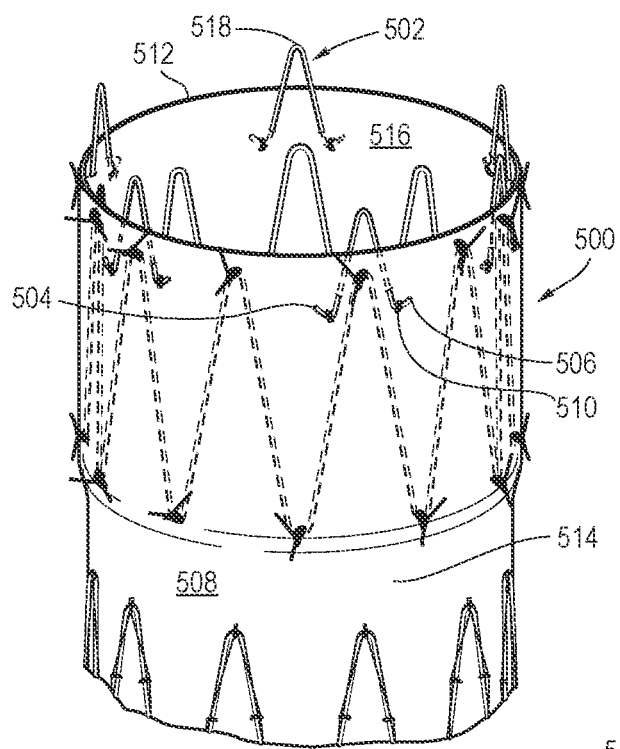
FIG. 5A illustrates an exploded partial perspective view of yet another example of a stent graft retention system including a plurality of discrete retention wire forms including first and second struts, attached to an outer surface of the stent graft, and apices extending past the inner (i.e., opposite) surface of a first edge of the stent graft.

Referring to FIG. 5A, an exploded partial perspective view of yet another example of a stent graft retention system 500 is illustrated. Stent graft retention system 500 includes a plurality of discrete retention wire forms 502 including first and second struts 504, 506 attached to an outer surface 508 of stent graft 514 by sutures 510. First and second struts 504, 506 pass through stent graft 514, such that apex 518 of the each discrete retention wire form 502 extends beyond a first edge 512 of inner surface 516 of stent graft 514. Though not shown in FIG. 5A, the plurality of discrete retention wire forms 502 may include first and second struts 504, 506 passing through stent graft 514 and attached to inner surface 516 of stent graft 514 by sutures 510, such that apex 518 of the each discrete retention wire form 502 extends beyond a first edge 512 of outer surface 508 of stent graft 514.

Figure 5B:
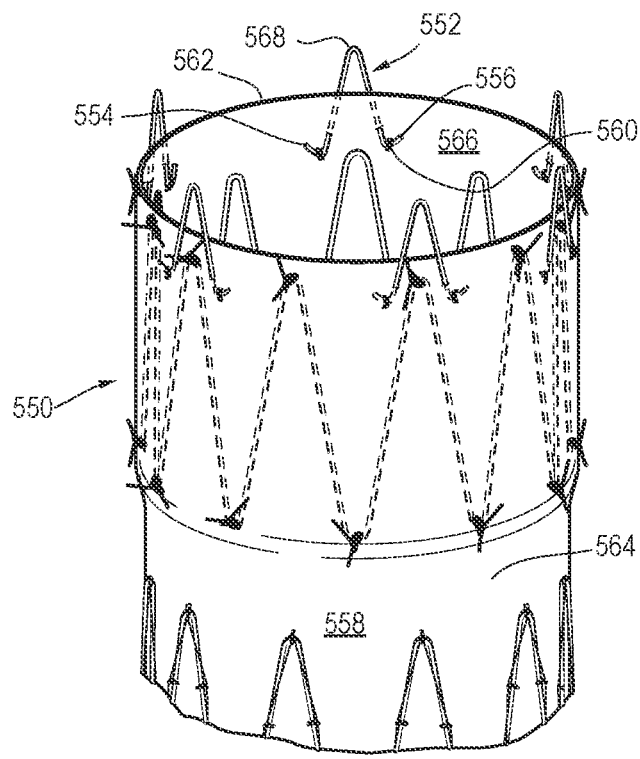
FIG. 5B illustrates an exploded partial perspective view of yet another example of a stent graft retention system including a plurality of discrete retention wire forms including first and second struts, attached to an inner surface of the stent graft, and apices extending past the outer (i.e., opposite) surface of a first edge of the stent graft.

Referring to FIG. 5B, an exploded partial perspective view of yet another example of a stent graft retention system 550 is illustrated. Stent graft retention system 550 includes a plurality of discrete retention wire forms 552 including first and second struts 554, 556 attached to an inner surface 566 of stent graft 564 by sutures 560. First and second struts 554, 556 pass through stent graft 564, such that apex 568 of the each discrete retention wire form 552 extends beyond a first edge 562 of outer surface 558 of stent graft 564.

Referring to FIG. 6A, an exploded partial perspective view of yet another example of a stent graft retention system 600 is illustrated. Stent graft retention system 600 includes stent graft 610 and retains stent graft 610 on a delivery device, such as a trigger wire. Stent graft retention system 600 further includes a plurality of discrete retention wire forms 620. Each discrete retention wire form 620 includes first loop 602, second loop 604, and wire 606 attaching first loop 602 and second loop 604. First loop 602 of the each discrete retention wire form 620 is attached to stent graft 610 a distance from first edge 608 by a suture 612 and second loop 604 extends beyond first edge 608. First loop 602 of the each discrete retention wire form 620 is attached to inner surface 614 of stent graft 610 between an apex 622 of first apices 622 of stent 618 and first edge 608. At least one of the plurality of discrete retention wire forms 620 is configured to engage a trigger wire at second loop 604. Though not shown in FIG. 6A, first loop 602 may be attached to one surface of stent graft 610, and second loop 604 may extend beyond first edge 608 of an opposite surface of stent graft 610 such that wire 606 passes through stent graft 610.

Referring to FIG. 6B, an exploded partial perspective view of yet another example of a stent graft retention system 650 is illustrated. Stent graft retention system 650 includes stent graft 660 and retains stent graft 660 on a delivery device, such as a trigger wire. Stent graft retention system 650 further includes a plurality of discrete retention wire forms 670. Each discrete retention wire form 670 includes first loop 652, second loop 654, and wire 656 attaching first loop 652 and second loop 654. First loop 652 of the each discrete retention wire form 670 is attached to stent graft 660 a distance from first edge 658 by a suture 662 and second loop 654 extends beyond first edge 658. First loop 652 of the each discrete retention wire form 670 is attached to outer surface 666 of stent graft 660. At least one of the plurality of discrete retention wire forms 670 is configured to engage a trigger wire at second loop 654.

Referring to FIG. 7A, an exploded partial perspective view of yet another example of a stent graft retention system 700 is illustrated. Stent graft retention system 700 includes stent graft 702 with eyelets 704. As shown in FIG. 7A, first and second struts 708, 712 of the plurality of discrete retention wire forms 720 pass through eyelets 704 such that first and second struts 708, 712 are attached to inner surface 718 of stent graft 702 by sutures 710 and apex 706 of the each discrete retention wire form 720 extends beyond first edge 714 of outer surface 716. Though not shown in FIG. 7A, first and second struts 708, 712 may pass through eyelets 704 such that first and second struts 708, 710 are attached to outer surface 716 of stent graft 702 and apex 706 of the each discrete retention wire form 720 extends beyond first edge 714 of inner surface 718.

Referring to FIG. 7B, an exploded partial perspective view of yet another example of a stent graft retention system 750 is illustrated. Stent graft retention system 750 includes stent graft 752 with eyelets 754. As shown in FIG. 7B, first and second struts 758, 762 of the plurality of discrete retention wire forms 770 pass through eyelets 754 such that first and second struts 758, 762 are attached to outer surface 766 of stent graft 752 by sutures 760 and apex 756 of the each discrete retention wire form 770 extends beyond first edge 764 of inner surface 768. First and second struts 758, 762 pass through eyelets 754 such that first and second struts 758, 762 are attached to outer surface 766 of stent graft 752 and apex 756 of the each discrete retention wire form 770 extends beyond first edge 764 of inner surface 768.

Referring to FIG. 8A, an exploded partial perspective view of an example of a stent graft retention system 800 is illustrated. Stent graft retention system 800 includes a plurality of discrete retention wire forms 812 attached to inner surface 818 of stent graft 802 at first and second struts 804, 806. As shown in FIG. 8A, first and second struts 804, 806 of the each discrete retention wire form 812 include loops. First and second struts 804, 806 of the each discrete retention wire form 812 are attached to stent graft 802 a distance from first edge 814 by sutures 810 such that apex 808 extends beyond first edge 814. As shown in FIG. 8A, apex 808 of the each discrete retention wire form 812 is "nested with" an apex 822 of the first apices 822 of stent 820, such that apex 808 and apex 822 may be coaxial and first and second struts 804, 806 are attached to stent graft 802 on opposite sides, circumferentially, of an apex 822 of the first apices 822 of stent 820.

Referring to FIG. 8B, an exploded partial perspective view of an example of a stent graft retention system 850 is illustrated. Stent graft retention system 850 includes a plurality of discrete retention wire forms 862 attached to outer surface 866 of stent graft 852 at first and second struts 854, 856. As shown in FIG. 8B, first and second struts 854, 856 of the each discrete retention wire form 862 include loops. First and second struts 854, 856 of the each discrete retention wire form 862 are attached to stent graft 852 a distance from first edge 864 by sutures 860 such that apex 858 extends beyond first edge 864.

Referring to FIG. 9A, an exploded partial perspective view of an example of a stent graft retention system 900 is illustrated. Stent graft retention system 900 includes stent graft 902 and retains stent graft 902 on a delivery device, such as a trigger wire. Stent graft retention system 900 further includes a plurality of discrete retention wire forms 918. Each discrete retention wire form 918 includes loop 906, hook 904, and wire 908 attaching loop 906 and hook 904. Hook 904 of the each discrete retention wire form 918 is attached to outer surface 916 of stent graft 902 a distance from first edge 912 by suture 910 and loop 906 extends beyond first edge 912. Hook 904 of the each discrete retention wire form 918 is attached to outer surface 916 of stent graft 902 between an apex 920 of first apices 920 of stent 922 and first edge 912. At least one of the plurality of discrete retention wire forms 918 is configured to engage a trigger wire at loop 906. Loop 906 extends beyond first edge 912 of inner surface 914 of stent graft 902 such that wire 908 passes through stent graft 902.

Referring to FIG. 9B, an exploded partial perspective view of an example of a stent graft retention system 926 is illustrated. Stent graft retention system 926 includes stent graft 928 and retains stent graft 928 on a delivery device, such as a trigger wire. Stent graft retention system 926 further includes a plurality of discrete retention wire forms 944. Each discrete retention wire form 944 includes loop 932, hook 930, and wire 934 attaching loop 932 and hook 930. Hook 930 of the each discrete retention wire form 944 is attached to inner surface 940 of stent graft 928 a distance from first edge 938 by suture 936 and loop 932 extends beyond first edge 938. Hook 930 of the each discrete retention wire form 944 is attached to inner surface 940 of stent graft 928 between an apex 946 of first apices 946 of stent 948 and first edge 938. At least one of the plurality of discrete retention wire forms 944 is configured to engage a trigger wire at loop 932. Loop 932 extends beyond first edge 938 of outer surface 942 of stent graft 928 such that wire 934 passes through stent graft 928.

Referring to FIG. 9C, an exploded partial perspective view of an example of a stent graft retention system 950 is illustrated. Stent graft retention system 950 includes stent graft 952 and retains stent graft 952 on a delivery device, such as a trigger wire. Stent graft retention system 950 further includes a plurality of discrete retention wire forms 968. Each discrete retention wire form 968 includes loop 956, hook 954, and wire 958 attaching loop 956 and hook 954. Hook 954 of the each discrete retention wire form 968 extends through stent graft 952 from inner surface 964 a distance from first edge 962 by suture 960, between an apex 970 of first apices 970 of stent 972 and first edge 962, and loop 956 extends beyond first edge 962 of inner surface 964. At least one of the plurality of discrete retention wire forms 968 is configured to engage a trigger wire at loop 956.

Referring to FIG. 9D, an exploded partial perspective view of an example of a stent graft retention system 976 is illustrated. Stent graft retention system 976 includes stent graft 978 and retains stent graft 978 on a delivery device, such as a trigger wire. Stent graft retention system 976 further includes a plurality of discrete retention wire forms 994. Each discrete retention wire form 994 includes loop 982, hook 980, and wire 984 attaching loop 982 and hook 980. Hook 980 of the each discrete retention wire form 994 extends through stent graft 978 from outer surface 992 a distance from first edge 988 by suture 986, between an apex 996 of first apices 996 of stent 998 and first edge 988, and loop 982 extends beyond first edge 988 of outer surface 992. At least one of the plurality of discrete retention wire forms 994 is configured to engage a trigger wire at loop 982.

Referring to FIG. 10A, an exploded partial perspective view of an example of a stent graft retention system 1000 is illustrated. Stent graft retention system 1000 includes stent graft 1002 and retains stent graft 1002 on a delivery device, such as a trigger wire. Stent graft retention system 1000 further includes a plurality of discrete retention wire forms 1018. Each discrete retention wire form 1018 includes loop 1006, strut 1004 including a "bar-bell" shape, and wire 1008 attaching loop 1006 and strut 1004. Strut 1004 of the each discrete retention wire form 1018 is attached to outer surface 1016 of stent graft 1002 a distance from first edge 1012 by suture 1010, and loop 1006 extends beyond first edge 1012. Suture 1010 is configured to attach strut 1004 to stent graft 1002 around a "bar" of each "bar-bell" shape. Strut 1004 of the each discrete retention wire form 1018 is attached to outer surface 1016 of stent graft 1002 between an apex 1020 of first apices 1020 of stent 1022 and first edge 1012. At least one of the plurality of discrete retention wire forms 1018 is configured to engage a trigger wire at loop 1006. Loop 1006 extends beyond first edge 1012 of inner surface 1014 of stent graft 1002 such that wire 1008 passes through stent graft 1002.

Referring to FIG. 10B, an exploded partial perspective view of an example of a stent graft retention system 1050 is illustrated. Stent graft retention system 1050 includes stent graft 1052 and retains stent graft 1052 on a delivery device, such as a trigger wire. Stent graft retention system 1050 further includes a plurality of discrete retention wire forms 1068. Each discrete retention wire form 1068 includes loop 1056, strut 1054 including a "bar-bell" shape, and wire 1058 attaching loop 1056 and strut 1054. Strut 1054 of the each discrete retention wire form 1068 is attached to inner surface 1064 of stent graft 1052 a distance from first edge 1062 by suture 1060, and loop 1056 extends beyond first edge 1062. Suture 1060 is configured to attach strut 1054 to stent graft 1052 around a "bar" of each "bar-bell" shape. Strut 1054 of the each discrete retention wire form 1068 is attached to inner surface 1064 between an apex 1070 of first apices 1070 of stent 1072 and first edge 1062. At least one of the plurality of discrete retention wire forms 1068 is configured to engage a trigger wire at loop 1056. Loop 1056 extends beyond first edge 1062 of outer surface 1066 of stent graft 1052 such that wire 1058 passes through stent graft 1052.

Referring to FIG. 11A, an exploded partial perspective view of an example of a stent graft retention system 1100 is illustrated. Stent graft retention system 1100 includes stent graft 1102 and a plurality of discrete retention wire forms 1112 including apex 1108 and first and second struts 1104, 1106, the first and second struts 1104, 1106 are attached to inner surface 1118 of stent graft 1102 by sutures 1110 such that apex 1108 extends beyond first edge 1114. First and second struts 1104, 1106 include hooks extending inward from inner surface 1118 of stent graft 1102. As shown in FIG. 11A, apex 1108 of the each discrete retention wire form 1112 is "nested with" an apex 1120 of first apices 1120 of stent 1122, such that apex 1108 and apex 1120 may be coaxial and first and second struts 1104, 1106 are attached to stent graft 1102 on opposite sides, circumferentially, of an apex 1120 of the first apices 1120 of stent 1122.

Referring to FIG. 11B, an exploded partial perspective view of an example of a stent graft retention system 1126 is illustrated. Stent graft retention system 1126 includes stent graft 1128 and a plurality of discrete retention wire forms 1138 including apex 1134 and first and second struts 1130, 1132, the first and second struts 1130, 1132 attached to outer surface 1142 of stent graft 1128 by sutures 1136 such that apex 1134 extends beyond first edge 1140. First and second struts 1130, 1132 include hooks extending outward from outer surface 1142 of stent graft 1128.

Referring to FIG. 11C, an exploded partial perspective view of an example of a stent graft retention system 1150 is illustrated. Stent graft retention system 1150 includes stent graft 1152 and a plurality of discrete retention wire forms 1162 including apex 1158 and first and second struts 1154, 1156, the first and second struts 1154, 1156 include hooks extending inward through stent graft 1152 from outer surface 1166. Sutures 1160 attach the first and second struts 1154, 1156 to outer surface 1166 of stent graft 1152. Apex 1158 of the each discrete retention wire form 1162 extends beyond first edge 1164 of outer surface 1166 of stent graft 1152. As shown in FIG. 11C, apex 1158 of the each discrete retention wire form 1162 is "nested with" an apex 1170 of first apices 1170 of stent 1172, such that apex 1158 and apex 1170 may be coaxial and first and second struts 1154, 1156 are attached to stent graft 1152 on opposite sides, circumferentially, of an apex 1170 of the first apices 1170 of stent 1172.

Referring to FIG. 11D, an exploded partial perspective view of an example of a stent graft retention system 1176 is illustrated. Stent graft retention system 1176 includes stent graft 1178 and a plurality of discrete retention wire forms 1188 including apex 1184 and first and second struts 1180, 1182, the first and second struts 1180, 1182 include hooks extending outward through stent graft 1178 from inner surface 1192. Sutures 1186 attach the first and second struts 1180, 1182 to inner surface 1192 of stent graft 1178. Apex 1184 of the each discrete retention wire form 1188 extends beyond first edge 1190 of inner surface 1192 of stent graft 1178.

Referring to FIG. 12, an exploded partial perspective view of yet another example of a stent graft retention system 1200 is illustrated. Stent graft retention system 1200 includes stent graft 1202. As shown in FIG. 12, at least one of the plurality of discrete retention wire forms 1206 engages trigger wires 302 of delivery device 306. Trigger wires 302 confront loop 1208 of each discrete retention wire form 1206. Trigger wires 302 each run out of one hole in nose cone 304 of delivery device 306 and into another hole. Nose cone 304 is connected to body 308 of delivery device 306. Trigger wires 302 continue into cannula 310 that passes through the center of the stent and stent graft 1202 parallel to a center longitudinal axis 312 of stent graft 1202. When trigger wires 302 of delivery device 306 engage the plurality of discrete retention wire forms 1206 at loop 1208, first edge 1204 of stent graft 1202 may close toward the center longitudinal axis 312.

Referring to FIG. 13A, a longitudinal end view of yet another example of a stent graft retention system 1300 is illustrated. Stent graft retention system 1300 includes a stent graft with a first edge 1302. Stent graft retention system 1300 includes three discrete retention wire forms 1304 disposed evenly around the circumference of an inner surface of the stent graft, at approximately 0°, 120°, and 240° relative to one another.

Referring to FIG. 13B, a longitudinal end view of yet another example of a stent graft retention system 1310 is illustrated. Stent graft retention system 1310 includes a stent graft with a first edge 1312. Stent graft retention system 1310 includes three discrete retention wire forms 1314 disposed unevenly around the circumference of an inner surface of the stent graft.

Referring to FIG. 13C, a longitudinal end view of yet another example of a stent graft retention system 1320 is illustrated. Stent graft retention system 1320 includes a stent graft with a first edge 1322. Stent graft retention system 1320 includes two discrete retention wire forms 1324 disposed evenly around the circumference of an inner surface of the stent graft, at approximately 180° relative to one another.

Referring to FIG. 13D, a longitudinal end view of yet another example of a stent graft retention system 1330 is illustrated. Stent graft retention system 1330 includes a stent graft with a first edge 1332. Stent graft retention system 1330 includes a discrete retention wire form 1334 disposed on the inner surface of the stent graft.

Referring to FIG. 14, an exploded partial perspective view of yet another example of a stent graft retention system 1400 is illustrated. Stent graft retention system 1400 includes stent graft 1402 and retains stent graft 1402 on a delivery device, such as a trigger wire. Stent graft 1402 includes first edge 1412 at a first end, and a stent 1418 including first apices 1422 and second apices 1424. First apices 1422 may be disposed adjacent the first end and second apices 1424 may extend in the direction opposite first edge 1412. Stent graft retention system 1400 further includes a plurality of discrete retention wire forms 1420. Each discrete retention wire form 1420 includes first strut 1404, second strut 1406, and apex 1408. First and second struts 1404, 1406 include loops. Apex 1408 of the each discrete retention wire form 1420 is attached to stent graft 1402 by sutures 1410 on outer surface 1414 of stent graft 1402 a distance from first edge 1412 such that first and second struts 1404, 1406 extend beyond first edge 1412. As shown in FIG. 14, apex 1408 of the each discrete retention wire form 1420 is "nested with" an apex 1424 of the second apices 1424, such that apex 1408 and apex 1424 may be coaxial. The each discrete retention wire form 1420 may be "A-shaped," with the "top" of the "A-shape" corresponding to apex 1408 and the "bottom" of the "A-shape" corresponding to first and second struts 1404, 1406. Apex 1408 may not necessarily be in the form of a sharp tip. Rather, first and second struts 1404, 1406 may extend away from apex 1408 in a non-parallel fashion.

Referring to FIG. 15A, an exploded partial perspective view of an example of a stent graft retention system 1500 is illustrated. Stent graft retention system 1500 includes stent graft 1510 and retains stent graft 1510 on a delivery device, such as a trigger wire. Stent graft retention system 1500 further includes a plurality of discrete retention wire forms 1520. Each discrete retention wire form 1520 includes first loop 1502, second loop 1504, and wire 1506 attaching first loop 1502 and second loop 1504. First loop 1502 of the each discrete retention wire form 1520 is attached to stent graft 1510 a distance from first edge 1508 by a suture 1512 and second loop 1504 extends beyond first edge 1508. First loop 1502 of the each discrete retention wire form 1520 is attached to inner surface 1514 of stent graft 1510 between two apices 1522 of first apices 1522 of stent 1518. At least one of the plurality of discrete retention wire forms 1520 is configured to engage a trigger wire at second loop 1504. Though not shown in FIG. 15A, first loop 1502 may be attached to one surface of stent graft 1510, and second loop 604 may extend beyond first edge 1508 of an opposite surface of stent graft 1510 such that wire 1506 passes through stent graft 1510.

Referring to FIG. 15B, an exploded partial perspective view of yet another example of a stent graft retention system 1550 is illustrated. Stent graft retention system 1550 includes stent graft 1560 and retains stent graft 1560 on a delivery device, such as a trigger wire. Stent graft retention system 1550 further includes a plurality of discrete retention wire forms 1570. Each discrete retention wire form 1570 includes first loop 1552, second loop 1554, and wire 1556 attaching first loop 1552 and second loop 1554. First loop 1552 of the each discrete retention wire form 1570 is attached to stent graft 1560 a distance from first edge 1558 by a suture 1562 and second loop 1554 extends beyond first edge 1558. First loop 1552 of the each discrete retention wire form 1570 is attached to outer surface 1566 of stent graft 1560. At least one of the plurality of discrete retention wire forms 1570 is configured to engage a trigger wire at second loop 1554.

Referring to FIG. 16A, an exploded partial perspective view of an example of a stent graft retention system 1600 is illustrated. Stent graft retention system 1600 includes stent graft 1602 and retains stent graft 1602 on a delivery device, such as a trigger wire. Stent graft retention system 1600 further includes a plurality of discrete retention wire forms 1618. Each discrete retention wire form 1618 includes loop 1606, hook 1604, and wire 1608 attaching loop 1606 and hook 1604. Hook 1604 of the each discrete retention wire form 1618 is attached to outer surface 1616 of stent graft 1602 a distance from first edge 1612 by suture 1610 and loop 1606 extends beyond first edge 1612. Hook 1604 of the each discrete retention wire form 1618 is attached to outer surface 1616 of stent graft 1602 between two apices 1620 of first apices 1620 of stent 1622. At least one of the plurality of discrete retention wire forms 1618 is configured to engage a trigger wire at loop 1606. Loop 1606 extends beyond first edge 1612 of inner surface 1614 of stent graft 1602 such that wire 1608 passes through stent graft 1602.

Referring to FIG. 16B, an exploded partial perspective view of an example of a stent graft retention system 1626 is illustrated. Stent graft retention system 1626 includes stent graft 1628 and retains stent graft 1628 on a delivery device, such as a trigger wire. Stent graft retention system 1626 further includes a plurality of discrete retention wire forms 1644. Each discrete retention wire form 1644 includes loop 1632, hook 1630, and wire 1634 attaching loop 1632 and hook 1630. Hook 1630 of the each discrete retention wire form 1644 is attached to inner surface 1640 of stent graft 1628 a distance from first edge 1638 by suture 1636 and loop 1632 extends beyond first edge 1638. Hook 1630 of the each discrete retention wire form 1644 is attached to inner surface 1640 of stent graft 1628 been two apices 1646 of first apices 1646 of stent 1648. At least one of the plurality of discrete retention wire forms 1644 is configured to engage a trigger wire at loop 1632. Loop 1632 extends beyond first edge 1638 of outer surface 1642 of stent graft 1628 such that wire 1634 passes through stent graft 1628.

Referring to FIG. 16C, an exploded partial perspective view of an example of a stent graft retention system 1650 is illustrated. Stent graft retention system 1650 includes stent graft 1652 and retains stent graft 1652 on a delivery device, such as a trigger wire. Stent graft retention system 1650 further includes a plurality of discrete retention wire forms 1668. Each discrete retention wire form 1668 includes loop 1656, hook 1654, and wire 1658 attaching loop 1656 and hook 1654. Hook 1654 of the each discrete retention wire form 1668 extends through stent graft 1652 from inner surface 1664 a distance from first edge 1662 by suture 1660, between two apices 1670 of first apices 1670 of stent 162, and loop 1656 extends beyond first edge 1662 of inner surface 1664. At least one of the plurality of discrete retention wire forms 1668 is configured to engage a trigger wire at loop 1656.

Referring to FIG. 16D, an exploded partial perspective view of an example of a stent graft retention system 1676 is illustrated. Stent graft retention system 1676 includes stent graft 1678 and retains stent graft 1678 on a delivery device, such as a trigger wire. Stent graft retention system 1676 further includes a plurality of discrete retention wire forms 1694. Each discrete retention wire form 1694 includes loop 1682, hook 1680, and wire 1684 attaching loop 1682 and hook 1680. Hook 1680 of the each discrete retention wire form 1694 extends through stent graft 1678 from outer surface 1692 a distance from first edge 1688 by suture 1686, between two apices 1696 of first apices 1696 of stent 1698, and loop 1682 extends beyond first edge 1688 of outer surface 1692. At least one of the plurality of discrete retention wire forms 1694 is configured to engage a trigger wire at loop 1682.

Referring to FIG. 17A, an exploded partial perspective view of an example of a stent graft retention system 1700 is illustrated. Stent graft retention system 1700 includes stent graft 1702 and retains stent graft 1702 on a delivery device, such as a trigger wire. Stent graft retention system 1700 further includes a plurality of discrete retention wire forms 1718. Each discrete retention wire form 1718 includes loop 1706, strut 1704 including a "bar-bell" shape, and wire 1708 attaching loop 1706 and strut 1704. Strut 1704 of the each discrete retention wire form 1718 is attached to outer surface 1716 of stent graft 1702 a distance from first edge 1712 by suture 1710, and loop 1706 extends beyond first edge 1712. Suture 1710 is configured to attach strut 1704 to stent graft 1702 around a "bar" of each "bar-bell" shape. Strut 1704 of the each discrete retention wire form 1718 is attached to outer surface 1716 of stent graft 1702 between two apices 1720 of first apices 1720 of stent 1722. At least one of the plurality of discrete retention wire forms 1718 is configured to engage a trigger wire at loop 1706. Loop 1706 extends beyond first edge 1712 of inner surface 1714 of stent graft 1702 such that wire 1708 passes through stent graft 1702.

Referring to FIG. 17B, an exploded partial perspective view of an example of a stent graft retention system 1750 is illustrated. Stent graft retention system 1750 includes stent graft 1752 and retains stent graft 1752 on a delivery device, such as a trigger wire. Stent graft retention system 1750 further includes a plurality of discrete retention wire forms 1768. Each discrete retention wire form 1768 includes loop 1756, strut 1754 including a "bar-bell" shape, and wire 1758 attaching loop 1756 and strut 1754. Strut 1754 of the each discrete retention wire form 1768 is attached to inner surface 1764 of stent graft 1752 a distance from first edge 1762 by suture 1760, and loop 1756 extends beyond first edge 1762. Suture 1760 is configured to attach strut 1764 to stent graft 1752 around a "bar" of each "bar-bell" shape. Strut 1754 of the each discrete retention wire form 1768 is attached to inner surface 1764 between two apices 1770 of first apices 1770 of stent 1772. At least one of the plurality of discrete retention wire forms 1768 is configured to engage a trigger wire at loop 1756. Loop 1756 extends beyond first edge 1762 of outer surface 1766 of stent graft 1752 such that wire 1758 passes through stent graft 1752.

Although the present disclosure has been described with reference to examples and the accompanying drawings, the present disclosure is not limited thereto, but may be variously modified and altered by those skilled in the art to which the present disclosure pertains without departing from the spirit and scope of the present disclosure.

The subject-matter of the present disclosure may also relate, among others, to the following aspects:

A first aspect relates to a stent graft retention system for retaining a stent graft on a delivery device, comprising: a stent graft comprising: a first end; a second end: a first edge at the first end; and a stent comprising first apices and second apices, the first apices disposed adjacent the first end and the second apices extending toward the second end; and a plurality of discrete retention wire forms each comprising a first strut, a second strut, and an apex between the first and second struts; wherein the first and second struts are attached to the stent graft a distance from the first edge and the apex extends beyond the first edge; wherein the each discrete retention wire form is nested with an apex of the first apices; and wherein at least one of the plurality of discrete retention wire forms is configured to engage a trigger wire.

A second aspect relates to the stent graft retention system of aspect 1, further comprising sutures configured to attach the first and second struts of the each discrete retention wire form to the stent graft.

A third aspect relates to the stent graft retention system of any preceding aspect, wherein the each discrete retention wire form is v-shaped.

A fourth aspect relates to the stent graft retention system of any preceding aspect, wherein the first and second struts of the each discrete retention wire form comprise flat hooks.

A fifth aspect relates to the stent graft retention system of any of aspects 1 to 3, wherein the first and second struts of the each discrete retention wire form comprise bar-bells.

A sixth aspect relates to the stent graft retention system of aspect 5, further comprising sutures configured to attach the first and second struts of the each discrete retention wire form to the stent graft; wherein the sutures are configured to attach the first and second struts around a bar of each bar-bell.

A seventh aspect relates to the stent graft retention system of any preceding aspect, wherein the first and second struts of the each discrete retention wire form are attached to the stent graft on a first surface of the stent graft and the apex of the each discrete retention wire form extends beyond the first edge of a second surface of the stent graft, the second surface opposite the first surface.

An eighth aspect relates to the stent graft retention system of aspect 7, wherein the first and second struts of the each discrete retention wire form pass through eyelets in the stent graft.

A ninth aspect relates to the stent graft retention system of any preceding aspect, wherein the plurality of discrete retention wire forms are disposed symmetrically about a circumference of the first edge.

A tenth aspect relates to a stent graft retention system for retaining a stent graft on a delivery device, comprising: a stent graft comprising: a first end; a second end; a first edge at the first end; and a stent comprising first apices and second apices, the first apices disposed adjacent the first end and the second apices extending toward the second end; and a plurality of discrete retention wire forms each comprising a first loop, a second loop, and a wire attaching the first loop and the second loop; wherein the first loop of the each discrete retention wire form is attached to the stent graft a distance from the first edge and the second loop extends beyond the first edge; wherein the first loop of the each discrete retention wire form is attached to the stent graft between an apex of the first apices and the first edge; and wherein at least one of the plurality of discrete retention wire forms is configured to engage a trigger wire.

An eleventh aspect relates to the stent graft retention system of aspect 10, further comprising sutures configured to attach the first loop of the each discrete retention wire form to the stent graft.

A twelfth aspect relates to the stent graft retention system of aspects 10 or 11, wherein the first loop of the each discrete retention wire form is attached to the stent graft on a first surface of the stent graft and the second loop of the each discrete retention wire form extends beyond the first edge of a second surface of the stent graft, the second surface opposite the first surface.

A thirteenth aspect relates to the stent graft retention system of aspect 12, wherein the wire of the each discrete retention wire form passes through an eyelet in the stent graft.

In addition to the features mentioned in each of the independent aspects enumerated above, some examples may show, alone or in combination, the optional features mentioned in the dependent aspects and/or as disclosed in the description above and shown in the figures.

What is claimed is:

1. A stent graft retention system for retaining a stent graft on a delivery device, comprising:
  a stent graft comprising:
    a first end;
    a second end;
    a first edge at the first end; and
    a stent comprising first apices and second apices, the first apices disposed adjacent the first end and the second apices extending toward the second end; and
  a plurality of discrete retention wire forms each comprising a first strut, a second strut, and an apex between the first and second struts;
  wherein the first and second struts are attached to the stent graft a distance from the first edge and the apex extends beyond the first edge;
  wherein each of the plurality of discrete retention wire forms is nested with an apex of the first apices, and the plurality of discrete retention wire forms nested with an apex of the first apices are less in quantity than the first apices; and
  wherein at least one of the plurality of discrete retention wire forms is configured to engage a trigger wire.

2. The stent graft retention system of claim 1, further comprising sutures configured to attach the first and second struts of each of the plurality of discrete retention wire forms to the stent graft.

3. The stent graft retention system of claim 1, wherein each of the plurality of discrete retention wire forms is v-shaped.

4. The stent graft retention system of claim 1, wherein the first and second struts of each of the plurality of discrete retention wire forms comprise hooks.

5. The stent graft retention system of claim 1, wherein the first and second struts of each of the plurality of discrete retention wire forms comprise bar-bells.

6. The stent graft retention system of claim 1, further comprising sutures configured to attach the first and second struts of each of the plurality of discrete retention wire forms to the stent graft;
  wherein the first and second struts of each of the plurality of discrete retention wire forms comprise bar-bells; and
  wherein the sutures are configured to attach the first and second struts around a bar of each bar-bell.

7. The stent graft retention system of claim 1, wherein the first and second struts of each of the plurality of discrete retention wire forms are attached to the stent graft on a first surface of the stent graft and the apex of each of the plurality of discrete retention wire forms extends beyond the first edge of a second surface of the stent graft, the second surface opposite the first surface.

8. The stent graft retention system of claim 1, wherein the first and second struts of each of the plurality of discrete retention wire forms are attached to the stent graft on a first surface of the stent graft and the apex of each of the plurality of discrete retention wire forms extends beyond the first edge of a second surface of the stent graft, the second surface opposite the first surface; and
  wherein the first and second struts of each of the plurality of discrete retention wire forms pass through eyelets in the stent graft.

9. The stent graft retention system of claim 1, wherein the plurality of discrete retention wire forms are disposed symmetrically about a circumference of the first edge.

10. The stent graft retention system of claim 1, wherein the first and second struts of each of the plurality of discrete retention wire forms comprise bar-bells; and
  wherein the first and second struts of each of the plurality of discrete retention wire forms pass through eyelets in the stent graft.

11. A stent graft retention system for retaining a stent graft on a delivery device, comprising:
  a stent graft comprising:
    a first end;
    a second end;
    a first edge at the first end; and
    a stent comprising first apices and second apices, the first apices disposed adjacent the first end and the second apices extending toward the second end; and
  a plurality of discrete retention wire forms each comprising a first strut, a second strut, and an apex between the first and second struts;
  wherein the first and second struts are attached to the stent graft a distance from the first edge and the apex extends beyond the first edge;
  wherein each of the plurality of discrete retention wire forms is nested with an apex of the first apices, and the plurality of discrete retention wire forms nested with the apex of the first apices are less in quantity than the first apices;
  wherein at least one of the plurality of discrete retention wire forms is configured to engage a trigger wire; and
  wherein the first and second struts of each of the plurality of discrete retention wire forms pass through eyelets in the stent graft and are attached to the stent graft on a first surface of the stent graft and the apex of each of the plurality of discrete retention wire forms extends beyond the first edge of a second surface of the stent graft, the second surface opposite the first surface.

12. The stent graft retention system of claim 11, further comprising sutures configured to attach the first and second struts of each of the plurality of discrete retention wire forms to the stent graft.

13. The stent graft retention system of claim 11, wherein each of the plurality of discrete retention wire forms is v-shaped.

14. The stent graft retention system of claim 11, wherein the first and second struts of each of the plurality of discrete retention wire forms comprise hooks.

15. The stent graft retention system of claim 11, wherein the first and second struts of each of the plurality of discrete retention wire forms comprise bar-bells.

16. The stent graft retention system of claim 11, further comprising sutures configured to attach the first and second struts of each of the plurality of discrete retention wire forms to the stent graft;
  wherein the first and second struts of each of the plurality of discrete retention wire forms comprise bar-bells; and
  wherein the sutures are configured to attach the first and second struts around a bar of each bar-bell.

* * * * *